United States Patent
Wang et al.

(10) Patent No.: US 11,419,756 B2
(45) Date of Patent: Aug. 23, 2022

(54) ATHLETE'S RECOVERY SYSTEM

(71) Applicant: XOTHRM LLC, Boise, ID (US)

(72) Inventors: Jo Han Wang, Boise, ID (US); Sean T. Whalen, Mountain View, CA (US)

(73) Assignee: Xothrm LLC, Boise, ID (US)

( * ) Notice: Subject to any disclaimer, the term of this patent is extended or adjusted under 35 U.S.C. 154(b) by 0 days.

(21) Appl. No.: 17/590,800

(22) Filed: Feb. 1, 2022

(65) Prior Publication Data

US 2022/0151822 A1    May 19, 2022

Related U.S. Application Data

(63) Continuation-in-part of application No. 17/402,390, filed on Aug. 13, 2021.

(60) Provisional application No. 63/065,328, filed on Aug. 13, 2020, provisional application No. 63/115,239, filed on Nov. 18, 2020.

(51) Int. Cl.
*A61F 7/00* (2006.01)
*A61N 5/06* (2006.01)

(52) U.S. Cl.
CPC ............ *A61F 7/007* (2013.01); *A61N 5/0625* (2013.01); *A61F 2007/0071* (2013.01); *A61F 2007/0078* (2013.01); *A61F 2007/0086* (2013.01); *A61F 2007/0088* (2013.01); *A61F 2007/0091* (2013.01); *A61F 2007/0093* (2013.01); *A61N 2005/0626* (2013.01); *A61N 2005/0645* (2013.01); *A61N 2005/0659* (2013.01)

(58) Field of Classification Search
CPC combination set(s) only.
See application file for complete search history.

(56) References Cited

U.S. PATENT DOCUMENTS

| | | | |
|---|---|---|---|
| 3,581,734 | A | 6/1971 | Croslin et al. |
| 4,494,534 | A | 1/1985 | Hutson |
| 4,682,588 | A | 7/1987 | Curlee |
| RE34,883 | E | 3/1995 | Grim |
| 6,057,530 | A | 5/2000 | Gurevich |
| 6,416,534 | B1 | 7/2002 | Montagnino et al. |
| 6,447,467 | B1 | 9/2002 | Barak |
| 6,591,142 | B1 | 7/2003 | Dea |
| 6,916,301 | B1 | 7/2005 | Clare |
| 7,891,019 | B2 | 2/2011 | Goldfine |
| 8,383,992 | B2 | 2/2013 | Wang et al. |
| 8,560,077 | B2 | 10/2013 | Feinstein |
| 8,579,953 | B1 | 11/2013 | Dunbar et al. |

(Continued)

FOREIGN PATENT DOCUMENTS

JP    H06231869 A    8/1994

OTHER PUBLICATIONS

Vatansever, Fatma, et al., "Far Infrared Radiation (FIR): Its Biological Effects and Medical Applications", Photonics Lasers Med., vol. 1, Nov. 1, 2012, pp. 255-266.

*Primary Examiner* — Joseph A Stoklosa
*Assistant Examiner* — Adam J Avigan
(74) *Attorney, Agent, or Firm* — Johnston IP Law, PLLC

(57) ABSTRACT

In one instance, a recovery system for a user is presented that includes a battery-operated, flexible wrap that applies heat with both conductive heat and radiant heat. The recovery system has a control unit that ramps the temperature applied using primarily perceived conductive heat before leveling at a target temperature. Other systems and devices are presented.

23 Claims, 18 Drawing Sheets

(56) References Cited

U.S. PATENT DOCUMENTS

| | | |
|---|---|---|
| 8,795,323 B2 | 8/2014 | Leschinsky |
| 8,945,027 B2 | 2/2015 | Batra et al. |
| 9,017,273 B2 | 4/2015 | Burbank et al. |
| 9,295,854 B2 | 3/2016 | Mersch |
| 9,907,692 B2 | 3/2018 | Binversie et al. |
| 10,660,790 B2 | 5/2020 | Barnett et al. |
| 10,736,766 B2 | 8/2020 | Booker |
| 2002/0026226 A1 | 2/2002 | Ein |
| 2006/0195168 A1* | 8/2006 | Dunbar ............... A61F 7/00 607/108 |
| 2008/0281307 A1 | 11/2008 | Donahue |
| 2011/0172750 A1 | 7/2011 | Cassidy et al. |
| 2012/0191164 A1 | 7/2012 | Gander et al. |
| 2013/0331914 A1 | 12/2013 | Lee et al. |
| 2014/0209594 A1 | 7/2014 | Besner |
| 2018/0193185 A1* | 7/2018 | Thomas ............... H05B 1/025 |
| 2019/0029877 A1 | 1/2019 | Betkowski |
| 2020/0246180 A1 | 8/2020 | Liang et al. |
| 2020/0383826 A1 | 12/2020 | Bayat |
| 2020/0404987 A1 | 12/2020 | Betkowski |

\* cited by examiner

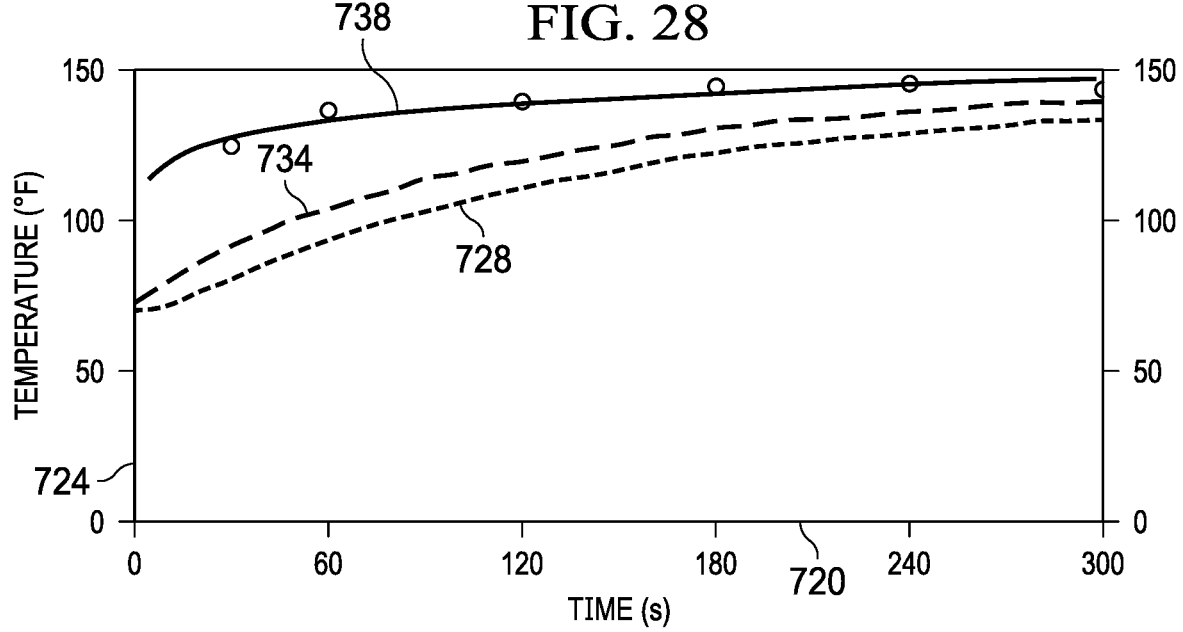

ATHLETE'S RECOVERY SYSTEM

CROSS-REFERENCE TO RELATED APPLICATION

This application is a continuation-in-part of U.S. Application Ser. No. 17/402,390 filed on Aug. 13, 2021, which claims the benefit of U.S. Provisional Application Ser. No. 63/065,328, filed by JoHan Wang et al., on Aug. 13, 2020, entitled "Athlete's Recovery System and Back Support" and U.S. Provisional Application Ser. No. 63/115,239, filed by JoHan Wang et al., on Nov. 18, 2020, entitled "Athlete's Recovery System and Support." The above-listed applications are incorporated herein by reference in their entirety for all purposes.

TECHNICAL FIELD

This application is directed, in general, to recovery systems, and more specifically, to systems, methods, and devices to assist with recovery from workouts or to address a portion of a user's body.

BACKGROUND

The following discussion of the background is intended to facilitate an understanding of the present disclosure only. It should be appreciated that the discussion is not an acknowledgement or admission that any of the material referred to was part of the common general knowledge at the priority date of the application.

After a person engages in exercise or other activity, it is desirable at times to take certain actions to expedite or facilitate recovery or comfort of the person's muscles. Some products have been developed to provide pain relief, support and even treat injury, edema and muscle or joint pain for portions of the body. While some systems and methods exist, improvements are desired.

SUMMARY

According to an illustrative embodiment, a portable, battery-powered recovery system for a human user includes a flexible wrap sized and configured to surround a portion of the user's body. The flexible wrap has a first side and a second side. The first side is outward facing when in an applied position and the second side is inward facing when in the applied position. The recovery system further includes a flexible-wrap fastener coupled to the flexible wrap for releaseably securing the flexible wrap around the portion of the user's body and at least one heating element coupled to the flexible wrap.

According to an illustrative embodiment, a portable, battery-powered recovery system for a user includes a flexible wrap sized and configured to surround at least a portion of the user's body to which a heating application is desired. The flexible wrap has a first side and a second side. The first side is outward facing when in an applied position and the second side is inward facing when in the applied position. The system further includes at least one heating element coupled to the flexible wrap and a control unit coupled to the flexible wrap and communicatively coupled to the at least one heating element for controlling the application of heat by the at least one heating element. The system further includes a battery coupled to the flexible wrap and electrically coupled to the at least one heating element. The control unit includes at least one processor and at least one non-transitory memory. The at least one non-transitory memory includes stored instructions, which when executed by the one or more processors, causes the controller to: to activate the at least one heating element to provide primarily conductive heat perceived by the user, and activate the at least one heating element to provide primarily infrared radiation heat.

According to still another illustrative embodiment, a portable recovery system for a user includes a flexible wrap sized and configured to surround at least a portion of the user's body. The flexible wrap has a first side and a second side. The first side is outward facing when in an applied position and the second side is inward facing when in the applied position. The system also has a flexible-wrap fastener coupled to the flexible wrap for releaseably securing the flexible wrap around the portion of the user's body and at least one heating element coupled to the flexible wrap. The system further includes a control unit coupled to the flexible wrap and to the at least one heating element for controlling the application of heat by the at least one heating element. The control unit and at least one heating element are configured to apply at least two modes of heat: conductive and radiant. The system also includes a power source coupled to the flexible wrap and electrically coupled to the at least one heating element and the control unit. The control unit includes at least one processor and at least one non-transitory memory. The at least one non-transitory memory has stored instructions, which when executed by the one or more processors, causes the controller to: to ramp power to the at least one heating element to provide primarily conductive heat perceived by the user, and to ramp down power to the at least one heating element to provide primarily infrared radiation heat. Other illustrative embodiments are referenced below.

DESCRIPTION OF THE DRAWINGS

Illustrative embodiments of the present invention are described in detail below with reference to the attached drawing figures, which are incorporated by reference herein and wherein:

FIG. 28 is a schematic graph of actual data (traces 728, 734) for an illustrative embodiment of a portable, battery-powered recovery system (such as system 100 in FIG. 3 or 400 in FIG. 14) that includes a flexible wrap for securing an at least one heating element and presented with temperature on the ordinate axis and time on the abscissa axis.

DETAILED DESCRIPTION

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the claims.

Unless otherwise indicated, as used throughout this document, "or" does not require mutual exclusivity.

At times athletes workout and desire treatment or comfort to assist with recovery. Athlete is used in a broad sense such as those who say if you have a body, you are an athlete. One way to assist is with pressure wrap that provides heat to the worked muscles while not sacrificing mobility. According to one aspect of the disclosure, a portable, battery-powered recovery system is presented and includes a flexible wrap that has a battery, controller, and heating element. It may further have a pneumatic-inflation-deflation subsystem. The recovery system controls the application of temperature and does so with contact controlled in part by pneumatic bladders that can be filled with a fluid (e.g., air) to apply pressure to a user or from which fluid may be removed to lessen pressure. In some embodiments, temperature modulation is practiced to avoid burning or irritating the user. Many other embodiments are possible, and some are presented below.

While at times the term "athlete" is used, it should be understood that the "user" may be anyone with a body: a client, patient, instructor, personal user, doctor, athletic trainer, coach, etc. Moreover, in an alternative embodiment, the user may be an animal, such as a racehorse.

Figure 1:
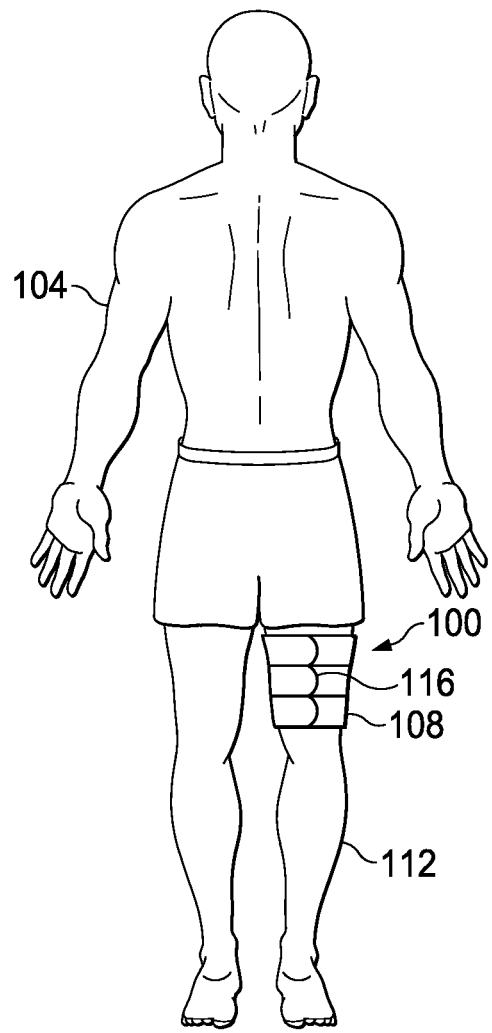
FIG. 1 is a schematic posterior view of a user with an illustrative embodiment of a recovery system applied to a user right leg.
Figure 2:
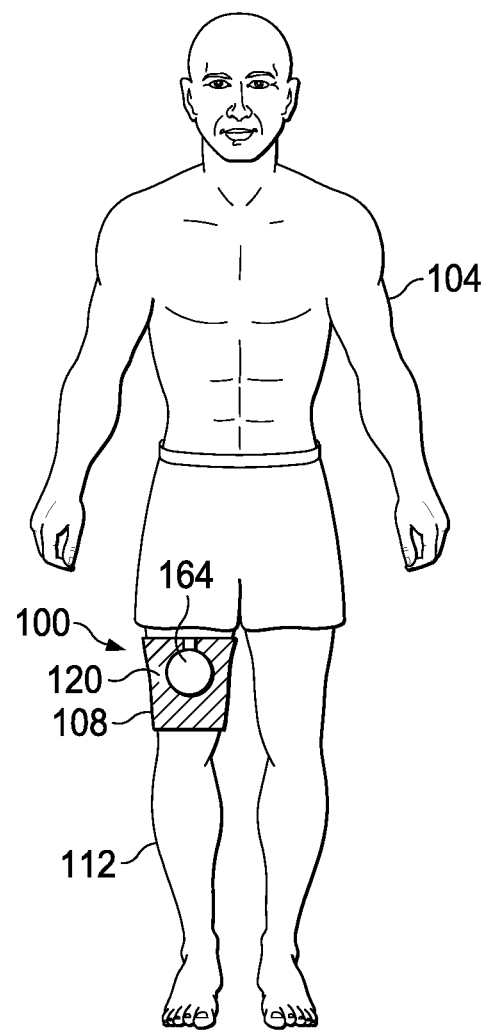
FIG. 2 is a schematic anterior view of a user with an illustrative embodiment of a recovery system applied to a user right leg.

Referring now to the figures and initially to FIGS. 1-2, a portable, battery-powered recovery system 100 for a human user 104 is presented. The portable, battery-powered recovery system 100 includes a flexible wrap 108, or garment, or pad, sized and configured to surround a portion of the user's body, e.g., leg 112. A flexible-wrap fastener 116 is coupled to the flexible wrap 108 for releaseably securing the flexible wrap 108 around the portion 112 of the user's body. The flexible wrap 108 is for securing an at least one heating element 128 in close proximity to a portion of the body of the user 104. While the portable, battery-powered recovery system 100 is shown used on the user's right leg, it should be understood that the system 100 may be used on any extremity or exterior body part as desired including, without limitation, torso, shoulders, and arms.

The flexible wrap 108 with the at least one heating element 128 on a heating-element insert 132 may be configured in any size, shape, thickness, and dimension as appropriate for wrapping around a specific portion of the user. A heating element assembly 134 comprises the at least one heating element 128 coupled to the heating-element insert. In one illustrative embodiment the heating element assembly 134 is 10 inches×12 inches and in another 11×15.5, but other dimensions may be used as one skilled in the art will understand. For example, in wrapping around an ankle the flexible wrap 108 may be 4 inches by 18 inches or another size. Further, the heating element assembly 134 may be non-rectangular, e.g., in a hexagonal pattern similar that seen on a soccer ball, which may promote folding around a joint such as a knee or shoulder. Other shapes and sizes may be used.

The heating element assembly 134 may be removable from the flexible wrap 108, or it may be permanently affixed to the flexible wrap 108. In the case that the heating element assembly 134 is removable, there may be a heating element attachment device such as a hook/loop fastener to releaseably connect the heating element assembly 134 to the flexible wrap 108 for ease of application to the user. One possible advantage of the heating element assembly 134 being removable is that the flexible wrap 108 may be washed, interchanged, or otherwise sterilized more quickly and simply between uses. Another possible advantage is that the power source of the heating elements, when using battery power, may be charged in a more compact charging station without the bulk of the flexible wrap 108 being permanently connected. The heating element attachment device may be button snaps, a hook-and-loop fastener, double-sided tape, a holster, or any suitable attachment means known to those skilled in the art.

Figure 3:
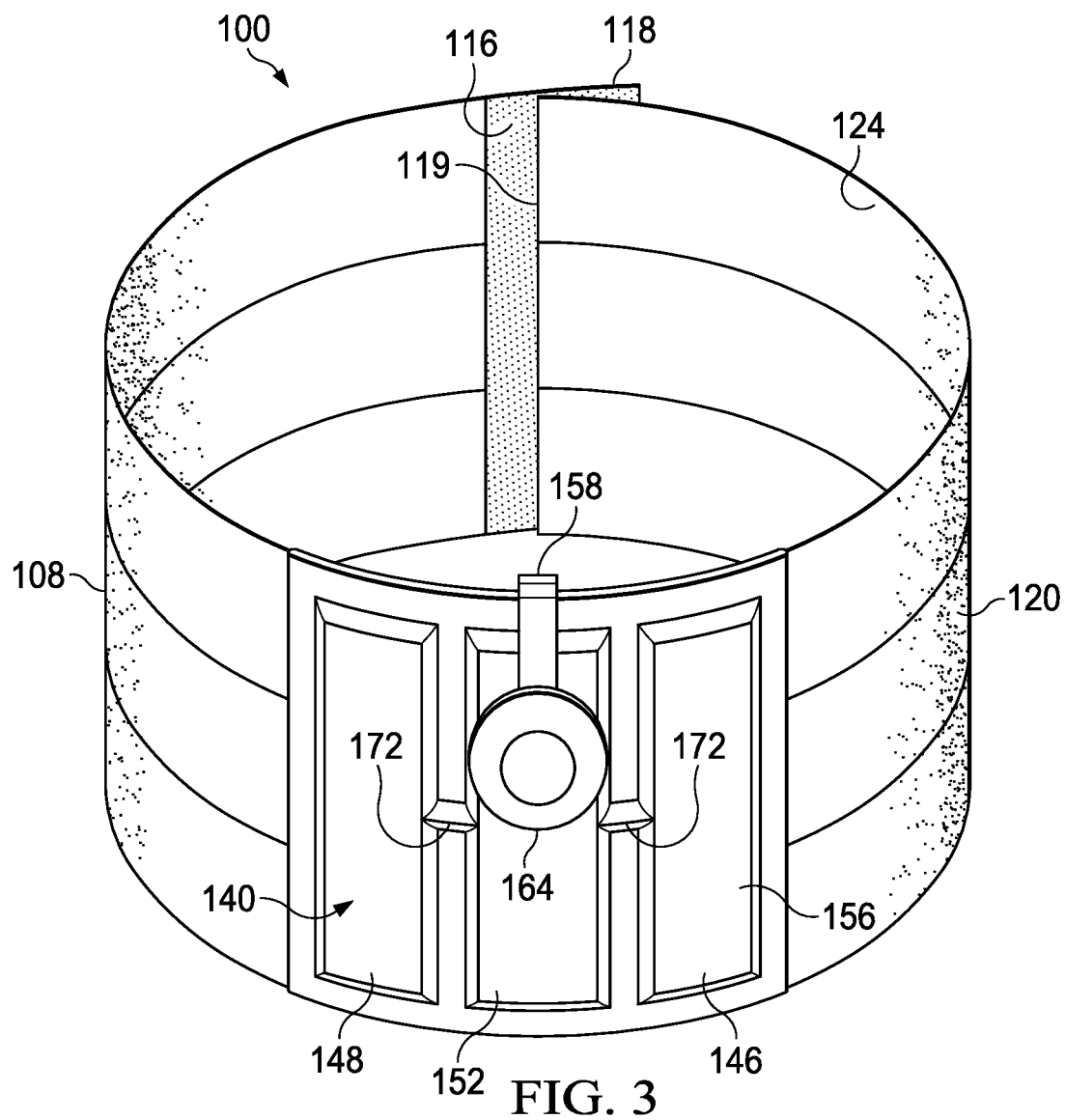
FIG. 3 is a schematic perspective view of an illustrative embodiment of a recovery system.
Figure 4:
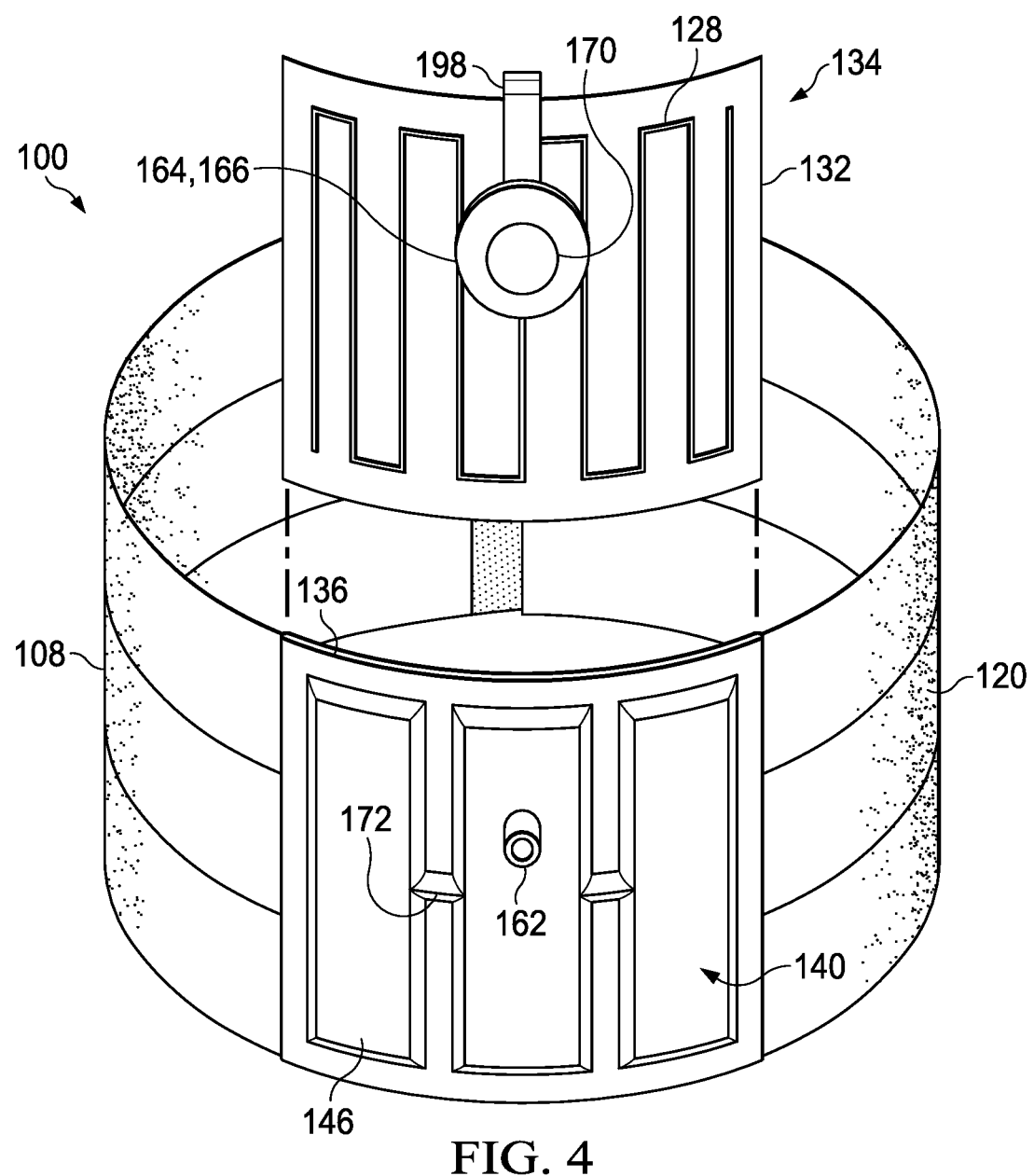
FIG. 4 is a partially exploded perspective view of the illustrative embodiment of a recovery system of FIG. 3.
Figure 5:
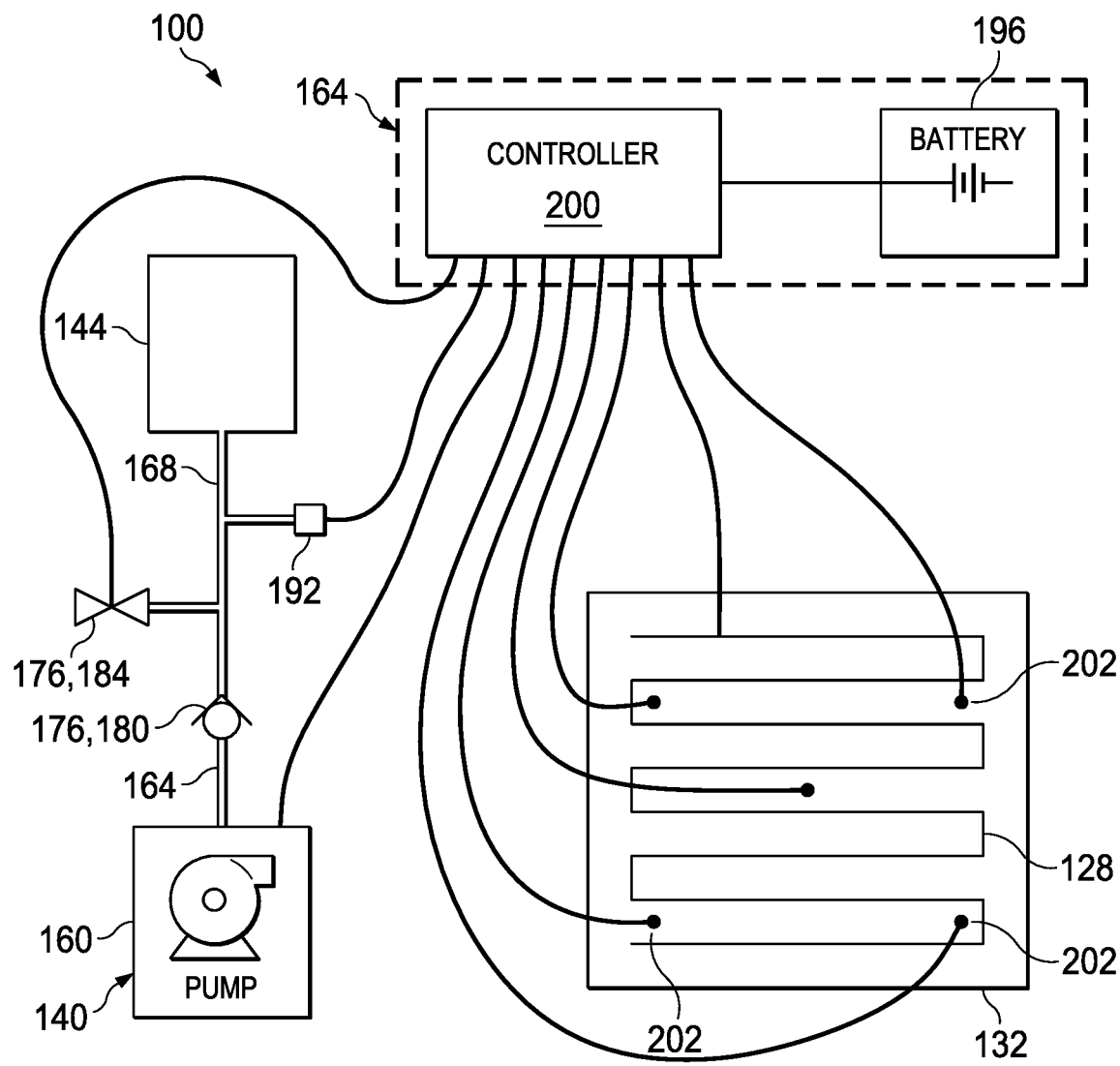
FIG. 5 is a schematic diagram of an illustrative embodiment of a recovery system without a flexible wrap.

Referring now primarily to FIGS. 3-5, the flexible wrap 108 has a first side 120 and a second, opposing side 124. The first side 120 is outward facing when in an applied position as shown in FIGS. 1-2 and the second side 124 is inward facing when in the applied position. The flexible-wrap fastener 116 is coupled to the flexible wrap 108 for reseleably securing the flexible wrap 108 around the portion 112 of the user's body. In some embodiments, the flexible wrap has a first end 118 and a second end 119 to which the flexible-wrap fastener 116 is attached for securing the flexible wrap in a circumference about a portion of the user's body. The flexible-wrap fastener 116 may take many forms, e.g., buttons, snaps, a zipper, magnets, hook-and-loop, high friction joint tri-glide style mechanism, glues or adhesives, ropes or knots, mechanical hooks, racks and pinions, high friction surfaces, or other fastener.

The flexible wrap 108 may be made of any suitable fabric or material that is flexible and may be non-stretch or stretch material or include elements that are elastic in nature for better accommodation of different size users. The flexible wrap 108 may be made from polyurethane coated fabrics, PVC coated fabrics or a similar material, urethane molds, latex rubber, stretch loop, SPANDEX material, or other materials.

The flexible wrap 108 may have a single wrapping segment or may have multiple wrapping segments. The wrapping segment wraps around a portion of the user's body and secures the recovery system 100 to the user 104. Alternatively, no wrapping segment may be needed and the recovery system 100 simply laid on top of a user and weighted down to apply pressure. In such case, the pneumatic bladder may be replaced with a weighting element (not shown), like a sandbag, which may be secured or slipped into a corresponding pocket on the flexible wrap 108. The at least one heating element 128 may also be designed to elongate, for example it may be an undulating pattern, sewn in between two sheets of stretch fabric whereby the parallel portions of the undulating pattern can move away from one another as the heating element is stretched. Such patterns and material combinations may be useful for contoured surfaces such as the knee, elbow, and shoulder to simultaneously provide good surface contact while also applying heat and compression.

At least one heating element 128 is coupled to the flexible wrap 108 to apply heat to the user 104. The at least one heating element 128 may be coupled to the heating-element insert 132 that is coupled to the flexible wrap 108 by direct attachment or within a pocket 136. Numerous devices and styles may be used as referenced below in connection with FIGS. 6-7.

The portable, battery-powered recovery system 100 may also include a pneumatic subsystem 140 that includes at least one pneumatic bladder 144, or compression element, coupled to the flexible wrap 108. The at least one pneumatic bladder 144 may be a plurality of pneumatic bladders 146 and in FIGS. 3-4 is shown as three pneumatic bladders 148, 152, 156.

The pneumatic subsystem 140 also includes at least one pneumatic pump 160 (FIG. 5), which in the illustrative embodiment of FIGS. 3-4 is part of a control unit 164, coupled to the flexible wrap 108 for selectively providing positive pressure to the at least one pneumatic bladder 144. The at least one bladder 144 may receive a fluid, e.g., air, by way of the pump 160 or another inflator. The control unit 164 allows for user input and controls the application of pneumatic pressure and temperature control as will be described further below.

The pneumatic subsystem 140 also includes one or more fluid conduits 168 (FIG. 5) fluidly coupled to the pneumatic bladder 144 and the pneumatic pump 160. If a plurality of pneumatic bladders 140 is used, one or more pneumatic conduits 172 may be used to fluidly couple the plurality of pneumatic bladders 146. With the pneumatic conduits 172, inflation of one inflatable bladder causes simultaneous inflation of all inflatable bladders and pressure is allowed to equalize between them for uniform compression against the user's body. Depending on the target part of the body of the recovery system 100, the size and shape of the inflatable bladders, or compartments, may change; in one illustrative embodiment, the size may be between 3 inches-5 inches in width and the height may be limited to between 6 inches-14 inches in height. Such dimensions allow for smaller systems to wrap around smaller parts of the body as well as larger systems to cover larger portions like a user's back. The width and height of the bladders may change across the length of the recovery system as well and may vary in width from about 1 inch to about 5 inches and in height from about 8 inches to about 14 inches. It may be desirable in a back wrap for example to have a larger bladder in the lower lumbar region with the width of adjacent bladders decreasing outboard away from the center bladder on both sides.

The pneumatic subsystem 140 may also include one or more pneumatic valves 176 associated with the fluid conduits 168 for controlling fluid flow therein; for example, the subsystem 140 may include one-way valve 180 and exhaust valve 184, which may be controlled by a signal from the control unit 164. In some embodiments, the exhaust valve 184 is a solenoid valve. The exhaust valve 184 may include quick-connect coupling valves, pressure relief valves, manual release valves, electromechanical valves, having gas flow shutoffs, not having gas flow shutoffs or other valves. Those skilled in the art will recognize that there are many variations of all these kinds of valves including mechanisms, materials, fabrication technique, sizes, port designs, and connectors that may be used. For example, a coupling valve may be configured for quick connect with locking means, such as a clasp, or break away means, or screw type, as some limited examples. The coupling valve may have a shutoff means to trap gas upon disconnection on one or both sides of the coupling valve, and the shutoff means may be any of such known mechanism including, but not limited to, duckbill valve, spring plunger, etc. Pressure relief valves and manual release valves similarly come in many shapes, sizes, materials, such as spring loaded, adjustable, non-adjustable, etc. Manual release valves further may be plunger style, screw on and off, pull tab release, rip cord release, etc. Electromechanical valves may be motor actuated, solenoid valves, or any other such valve that employs electric current to open and close.

In another illustrative embodiment, the valves may be manually operated or may simply be a single set pressure and relief valve at pre-set value which would eliminate the need for the pressure sensor 192.

In one alternative embodiment, an inflator may be used in addition to the pump 160 or in place of the pump 160. In such an embodiment, an air (or other fluid) reservoir may also be connected to the conduits of the wrap 108 so that when the controller 200 is commanded to inflate, it may release the fluid reservoir into the wrap 108 immediately to fill or bolster the pumping from the electromechanical pneumatic pump 160, which may be desired to be small, quiet, and therefore provide lower flow than would otherwise be desired.

The portable, battery-powered recovery system 100 also includes the control unit 164 coupled to the flexible wrap 108 and coupled in a control sense to the pneumatic subsystem 140 and to the at least one heating element 128 for controlling inflation and deflation of the pneumatic bladders in the pneumatic subsystem 140 and the application of heat by the at least one heating element 128. The pneumatic subsystem 140 may include a pressure sensor or transducer 192 that provides a pressure signal to the control unit 164.

The portable, battery-powered recovery system 100 includes a battery 196 (or batteries in some embodiments) coupled to the flexible wrap 108 and electrically coupled to the pneumatic subsystem 140 and to the at least one heating element 128. The control unit 164 may comprise the battery 196. The battery 196 may be a lithium-ion battery, lithium polymer, acid batteries, cadmium batteries, metal hydride batteries, other types. In some embodiments, the battery or batteries 196 are encased in plastic. The battery or batteries 196 may be removeable and separated for transportation.

The control unit 164 may be coupled to the heating element insert 132 or heating element assembly 134. In some embodiments, the control unit 164 is coupled to the pneumatic pump 160 to form a control assembly 166 that may be coupled such as by an offset arm 198 to the heating element assembly 134 (FIGS. 3 and 4). The control assembly 166 may present control selectors, e.g., push buttons, or indicators, e.g., present a temperature, towards the user on a front face 170 and may have the pneumatic pump 160 attached to a rear face, which is opposite the front face 170. In this embodiment, the output of the pump 160 is fluidly coupled to pressure input port 162 (FIG. 4) on the at least one pneumatic bladder 144.

The input port 162 may be any suitable device for attaching to the pump or inflator. The connection at the input port 162 may be done with threads, quick disconnects, friction, interference fit, or other connectors as one skilled in the art will appreciate. The location and size of the inflatable bladders may be tailored to the intention of the recovery system 100, such that the recovery system 100 may remain flexible and wrap easily and contour to the user's body around joints and small diameter appendages.

In some embodiments, the controller unit 164 may be removable to allow for more efficient charging configurations in embodiments in which the system 100 includes rechargeable batteries. In the case of permanent attachment, the heating element assembly 134 may be connected to the flexible pad 108 via stitching, gluing or otherwise captured within a pocket. In another illustrative embodiment, the flexible wrap 108 is configured such that folding the wrap 108 over the heating element assembly 134 is sufficient to hold the heating element assembly 134 in place and further secure it in close proximity to the user 104. In this embodiment, anti-slip pads or grips may be attached to the side facing the user and aid in preventing the at least one heating element 128 from slipping within the wrap 108.

Referring now primarily to FIG. 5, aspects of the portable, battery-powered recovery system 100 are presented in a schematic form. In this view, one may see that the control unit 164 includes a controller 200 and one or more batteries 196. The control unit 164, and more specifically the controller 200 is communicatively coupled to the pneumatic subsystem 140 such as to the pump 160, pressure sensor 192 and the exhaust valve 184. One may also see that the least one heating element 128 is electrically coupled to the control unit 164 and the heating-element insert 132 may include a plurality of thermal transducers or thermocouples 202 that are also communicatively coupled to the control unit 164. While five thermocouples 202 are shown, it should be understood that one thermocouple could be used or many more thermocouples could be used, e.g., 2-10 or more.

One or more thermocouples 292 may be placed on the flexible wrap 108 from a safety perspective to prevent the flexible wrap 108 from overheating and possibly burning or irritating a user 104. Because the flexible wrap 108 may be intentionally overpowered or ramped (see, e.g., FIG. 11) in order to apply perceived heat at the outset, a safety monitoring system, or temperature monitoring routine (see, e.g., FIG. 13) may be desirable. In order to ensure that the temperature sensor(s) or thermocouple(s) 202 that is being relied upon in that safety monitoring system is reading maximum skin temperature, a physical bump or outward dentation or probe offsets may be applied behind the temperature sensor or thermocouple 202 so that the thermocouple 202 is closer to the skin surface of the user 104 than the rest of the inner most surface. To the extent multiple temperature sensors 202 are used, each such sensor 202 may have a raised bump or backing behind it. Whereas the heating pad may be generally made of flat layers, the bump may be a semi-rigid or rigid object in-between the heating element layer and a next-outermost layer, thereby pushing that portion of the heating element, as well as the temperature sensor 202, closer to the skin of the user 104 than the rest of the innermost surface.

In some embodiments, the bump is molded into an inner most layer. In some embodiments, the bump is a separate item sandwiched inside the flexible wrap 108. In the case of pneumatic chambers or bladders 144 being used in the heating pad, these pneumatic bladders 144, and an apex formed when the bladder is inflated, may serve as the bump or portion of the flexible wrap that pushes the temperature sensor 202 closer to the skin. In this case the temperature sensor(s) 202 would be placed on or near the inward apex of an inflatable bladder, or otherwise at a point that pushes against the body of the user 104 the hardest and therefore provides the highest skin temperature for feedback to the temperature control safety system.

All the components shown in FIG. 5 may be coupled to the flexible wrap 108 by direct coupling with glue, or by inserts with fastening devices, e.g., hook-and-loop material, or inserting into pockets formed on the flexible wrap or by having compartments and a mechanically latch. In some embodiments, the control unit 164 may be part of the heating element assembly 134 or coupled to the heating element assembly 134.

The heating element assembly 134 may include an optionally removable controller 200 as part of the control unit 164. The controller 200 may control all the electronic elements in the recovery heating system 100, or alternatively control some. The controller 200 may include a processor such as, but not limited to, a microcontroller or microcomputer. The controller 200 is described further below in connection with FIG. 9.

Figure 6:
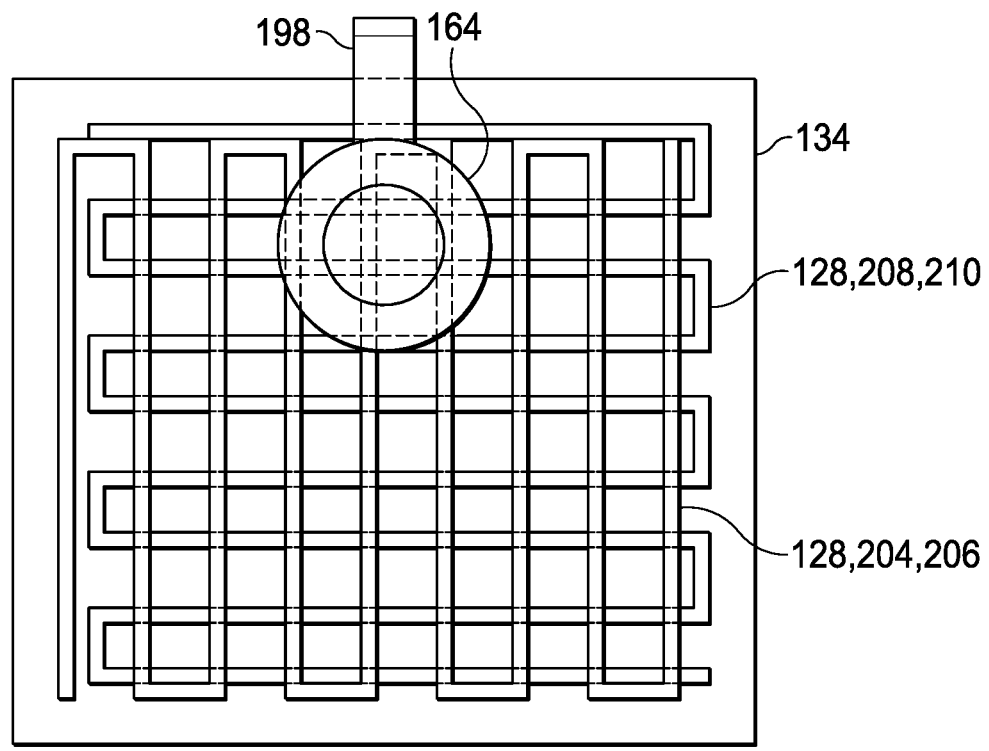
FIG. 6 is a schematic plan view of a heating element assembly for use as an aspect of a recovery system.

Referring now primarily to FIG. 6, an illustrative embodiment of a heating element assembly 134 is presented. In this embodiment, the at least one heating element 128 comprises a first heating element 204 and a second heating element 208.

The first heating element 204 may comprise a radiating heating element 206 that may be formed from any suitable material that is known to emit Far Infrared Waves (FIR heating) via black body radiation. Such material may be, but is not limited to, carbon fiber wiring wrapped in an undulating pattern as shown in FIG. 6. Other such radiating bodies may be similarly used to produce FIR heating. The second heating element 208 of the heating element assembly 134 may be a conduction heating element 210 made of a suitable material used to produce heat transfer through conduction. Such a heating element 210 may be, but is not limited to, a copper or steel wire formed in an undulating pattern as shown.

The layout pattern of the source of heat, first heating element 204 and second heating element 208, is shown as an undulating cable but the pattern may be any such pattern that produces heat in a desired location on the target area of the user. For example, the pattern may be circular, rectangular, polygon, star shaped, or other shaped. The pattern may involve having a portion of the flexible wrap 108 covered and a portion uncovered. Those skilled in the art will appreciate that many patterns may be used for different locations and applications of the recovery system 100. Further, a heating element assembly 134 may include both a radiating heating element 206 and a conduction heating element 210, or only one of them. A benefit of including both is that the conduction heating element 210 provides better "perceived" heat to the user 104, meaning the user feels the heat more, whereas a radiating heating element 206 may provide deeper heat penetration which is not felt per say by the user 104 but is more effective at deep heating the soft tissue. The heating element may also be a conductive medium such as conductive rubber, cloth or carbon fiber wool.

The arrangement of the radiating heating element 206 and the conduction heating element 210 may be such that the heat producing portion is co-planar or stacked directly on top with patterns in different directions. The two heating elements 206, 210 are depicted as coils, each in an undulating pattern, but rotated 90 degrees from one another.

Figure 7:
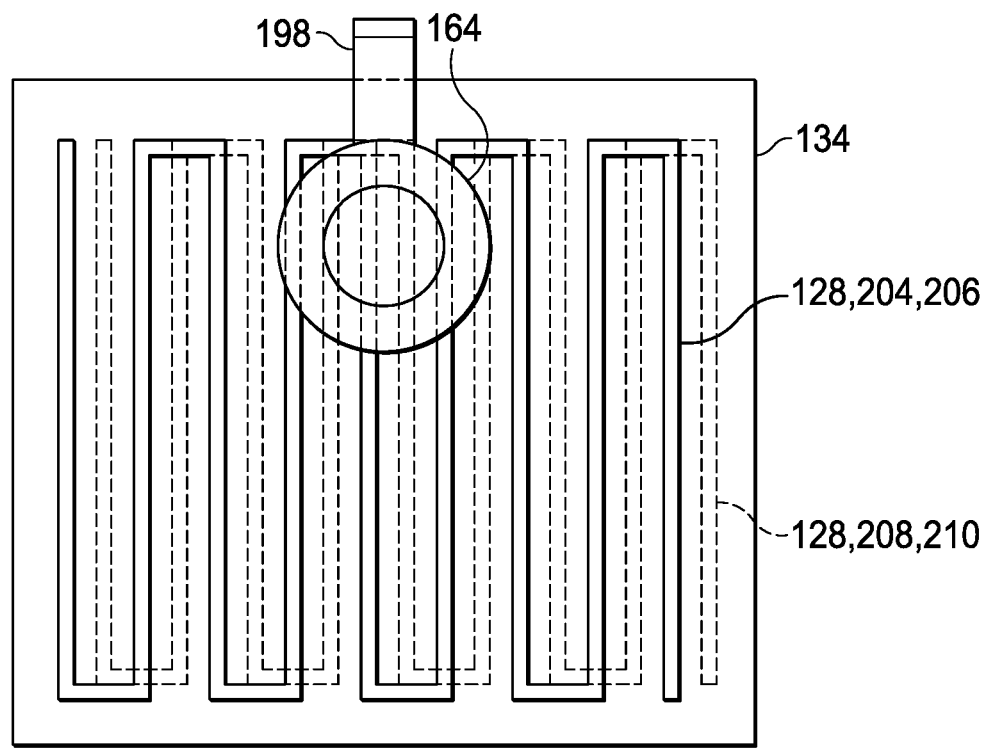
FIG. 7 is a schematic plan view of another heating element assembly for use as an aspect of a recovery system.

As shown in FIG. 7, the arrangement of the radiating heating element 206 and the conduction heating element 210 may be purposefully offset from one another. The figure shows two heat-production portions, the radiating heating element 206 and the conduction heating element 210, that are offset by a certain amount, e.g., a distance of at least 0.125 inches in some embodiments. Offsetting or reorienting the two heating-production portions, the radiating heating element 206 and the conduction heating element 210, in the case that there are two such elements in the heating element assembly 134 may have the advantage of better heat distribution over the limb or desired area and less risk of burning or irritating the skin.

The heating portion, whether it be a radiating heating element 206 or a conduction heating element 210 or both, may be captured in or disposed within an enclosure or pocket 136 (FIG. 4) and may be held in a sleeve. The pocket 136 may be fabric or may be a plastic based material that can be sterilized. In the case in which the heating element assembly 134 is removable from the flexible wrap 108, the pocket 136 and sleeve can be sterilized and that may offer a distinct advantage in scenarios with high user throughput like an athletic training room. The sleeve that goes in the pocket 136 or the pocket 136 itself may capture the conduction heating element 210 or radiating heating element 206, or both with stitching or simply glue or a fastener, sandwiched between two plastic sheets that are welded or sewn together, or any other suitable fastener. The pocket 136 locks the radiating heating element 206 and a conduction heating element 210 that provide heat into a fixed geometry and construction to ensure that they apply heat as desired.

In one illustrative embodiment, the heating means, e.g., the conductive heating element or the radiating heating element, may be positioned to heat different areas of the system 100 to different temperatures. For example, in one embodiment, the heat applied to a muscular area may be different than that applied to a bone portion.

While the heating element 128 is shown as a coil 206, 210 that is conductive or radiating in FIGS. 6 and 7, in some embodiments, a conductive sheet, e.g., a conductive rubber, is used, for one or both. In one illustrative embodiment, the system 100 uses far infrared (FIR). Far infrared radiation is often defined as a subdivision of the electromagnetic spectrum in the range of 3-100 micrometers. FIR penetrates much deeper—in some instances as much as 8 to 10 times deeper than mere conduction heat. FIR is a better heating modality for helping with recovery—better than conducting, surface-based heat transfer. One possible issue, however, with the user experience has to do with the user's experience of a sensation of heat.

With FIR alone, the user may not feel heat and in a psychological sense may believe that nothing is happening. FIR, in general, runs at a much lower temperature because it is driven by radiation, which works by heating from the inside out, heating deeper. Conversely, conductive heat is superficial in nature, which stimulates the heat thermoreceptors found in the skin. This broadcasts the perception of heat to the brain for a different user experience or perception. The system 100 addresses the heat perception issue by providing a sensation of heat through conductive heat. In one aspect, the present disclosure addresses this issue by using both conduction and radiant heat. In some embodiments, this is done with a single, dual-function heating element and in another by having two separate heating elements: one conduction and radiant.

In one illustrative embodiment, a material, such as a conductive elastomer or rubber sheet, may be used to provide the heat. The conductive sheet may be a rubber with a metal or other conductive particles added such as silver, nickel, silvered glass, silvered aluminum, or graphite. In other embodiments, the conductive sheet may comprise an oriented wire in a solid silicone, metalized filled silicones, wire screen embedded into silicone, conductive fabric, carbon fiber wool, or other material.

A carbon fiber wire is an efficient emitter of FIR radiation but not a great conductor, therefore multiple circuits of wire may be required analogous to the multiple panels described herein. Metal wire may be a good conductor of electricity and superficial heating, but may be a poorer generator of FIR radiation. Whereas energizing a wire is straightforward, conductive sheets may generally have electricity passed through them from one side to the other via conductive bus bars coupled at opposite ends of the sheet. A positive voltage is applied to one bus bar and a negative voltage to the other, and current is then driven across the conductive sheet via this voltage differential. A conductive sheet may offer advantages in terms of more even complete heating than a wire because current is passing through the entire surface area vs an undulating pattern that only covers a fraction of the surface area. A wire type of conductor may have an advantage where multi-degree articulation is required or where bus bars may not be easily applied parallel to one another which can cause un-even heating across a conductive sheet. The at least one heating element 132 is meant to include either approach.

In the case wiring is used, a conductive heat transfer material wire (e.g., copper) may run in parallel with a principally FIR radiating material (e.g., carbon fiber) and the conductive wire energized in the beginning stage of the session, for example for 1-2 min, to apply a noticeable and perceivable heat to the surface of the body, and then turned off while the principally FIR generating material is energized. The energization of the two materials may additionally overlap so there is a smooth transition between principally conductive heat transfer and principally FIR radiation heat transfer.

With a conductive sheet, the heat is initially ramped with relatively high power applied such that the material produces a conductive heat that allows the user to superficially experience heat—heat at a level that might not be sustainable for a long treatment. After that, the power applied is lowered such that the material provides heat through FIR. It should be understood that in the power variations, both conductive and radiant heat are developed but the proportions can be impacted by the power regiment. The initial "heat ramp" allows the user to experience an initial heat sensation while FIR is used for deeper treatment. This kind of pattern in shown in FIG. 11, which is described further below. In one illustrative embodiment, to cause the conductive material to generate the conductive heat, the system 100 may provide a significant amount of power to the conductive material, e.g., 50-100 watts for about 1-2 minutes, and then it is ramped down. Other power settings and durations may be used in other applications as one skilled in the art will perceive from this disclosure. In another illustrative embodiment, this ramping-decreasing pattern is repeated periodically. Ramp means to increase quickly in the power on mode or decrease in the power reduction or off mode.

In should be appreciated that many, if not all, heating elements have both some degree of conductive and radiation heat transfer involved. With some materials referenced there is an increase in temperature as the emissivity drops. In that case, the additional heat is going to conduction or convection. By increasing power with these materials, a shift towards more conduction is made. The wavelength of peak emissivity decreases with increasing temperature for most all materials, and this means shorter wavelengths, which penetrate less and stay closer to the skin (nerves), result. Again, while not limited by theory, it is believed that the higher applied power is raising the temperature of the heating element, which is reducing the wavelength of the radiation emissions and bringing more heat closer to the skin surface of the user, and that in turn stimulates nerves and alerts the user that the device is working.

Figure 8:
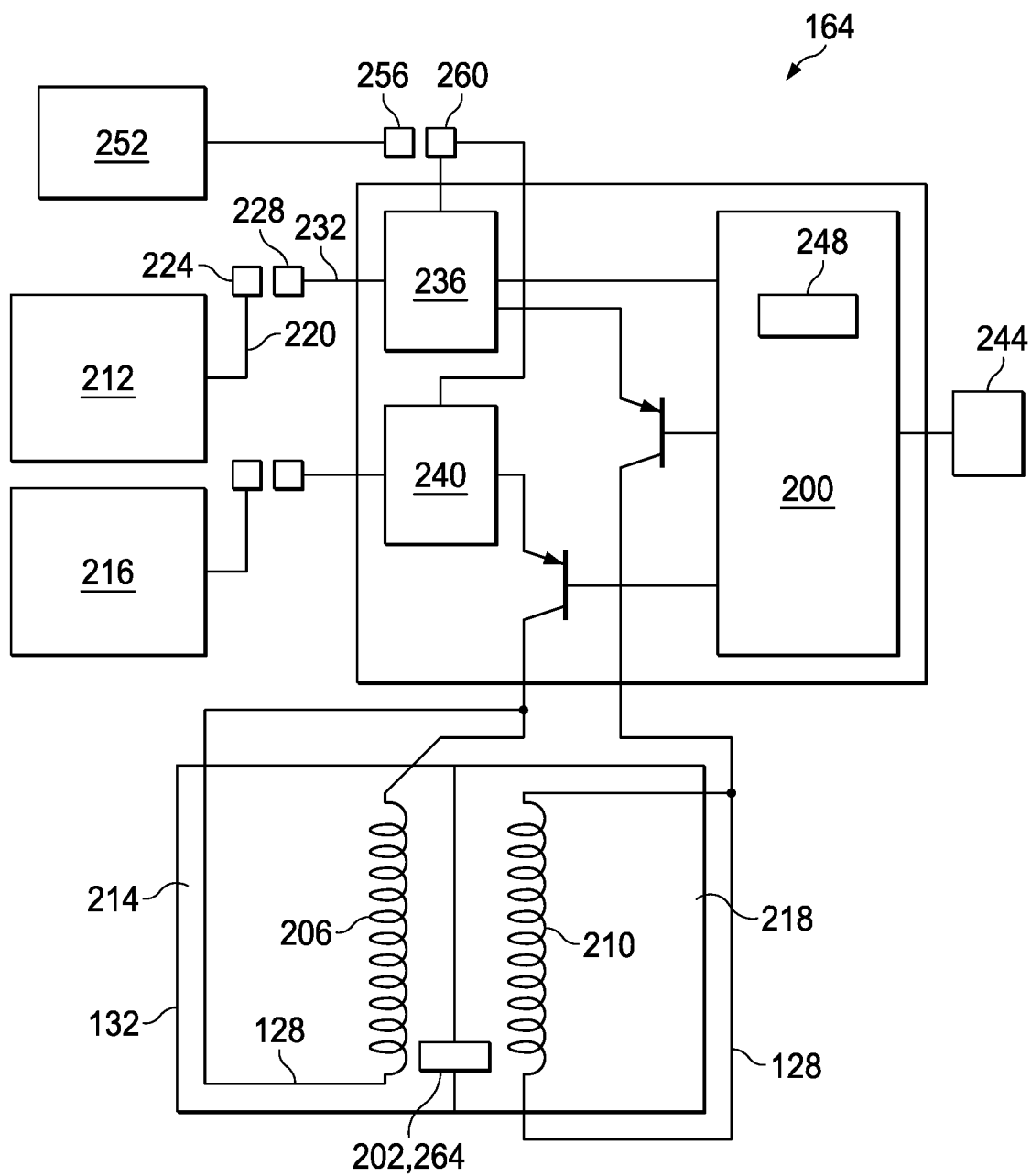
FIG. 8 is a schematic circuit diagram of an illustrative embodiment of a circuit and electrical components for a recovery system.

Referring now primarily to FIG. 8, one illustrative embodiment of the control unit 164 is presented. The control unit 164 includes a plurality of batteries, e.g., batteries 212 and 216, each with a conduit and coupler; for example, battery 212 has electrical conduit 220 with connector 224. While two batteries are shown, it should be understood that in other embodiments there may be only one battery and in still others there may be three or more. The connectors mate with connectors on an input conduit; for example, the connector 224 mates with a complimentary coupler 228 on electrical conduit 232 going to a first battery charge/discharge circuit 236. In some embodiments, the charge/discharge circuit 236 is included with the batteries 212, 216.

An analogous arrangement exists for the second battery 216 going to a second battery charge/discharge circuit 240. The battery charge/discharge circuits 236, 240 are electrically coupled to the controller 200 and the heating elements 204, 208 on the insert 132. The controller 200 has on/off switch 244 and may have other inputs such as temperature setting or heat setting (high, medium, low) or other settings and controls and displays, e.g., display 248. The display 248 may be LEDs showing battery charge status. A power source 252, e.g., from a wall socket, may be used for providing energy for charging through complimentary couplings 256, 260. A thermocouple 202, e.g., a thermistor 264, may be included for providing input to the controller 200.

With reference still to FIG. 8, the at least one heating element 128 is shown as two separate heating elements 206, 210, but in other embodiments, it is one conductive material but with a plurality of panels, e.g., two panels 214, 218. To get the desired temperature ramp, the resistance across the at least one heating element 128 may need to be effectively lowered. This is to allow enough current through it to get the high heat ramped temperature. If the flexible wrap is 11.5 and 15 inches—in a coil or conductive rubber—there is current across the whole area. The more area, the more heating element 128 is needed, but the more resistance. Using a conductive sheet and breaking the conductive sheet into panels, e.g., 214, 218, and running voltage in parallel helps with this issue. Cutting the panel allows more current because the resistance is down. While two panels 214, 218 are shown (and functionally shown as coils in the circuit) it should be understood that more or less panels may be used, e.g., 1, 3, 4, 5, 6, etc.

Still referring to FIG. 8 and said a different way, in one illustrative embodiment, the heating element 132 may be broken up into two or more conductive panels, e.g., 214, 218. In order to achieve a faster heat ramp without requiring larger, non-standard batteries (or battery), a low resistance value for each conductive panel may be desired because the battery voltage may practically be limited between, for example, 7.4-15V. Therefore, in this embodiment, in order to draw enough amperage to provide rapid heat—or heat ramping, the resistance of each panel or pad may need to be on the order of for example 1-8 Ohms. However, depending on the area required to be heated, a larger area will require a larger heating element material and the larger the heating element material the more resistance it has for passing electricity through that material. Therefore, breaking up the area into multiple panels, e.g., 214, 218, may allow each panel to have a resistance value appropriate for fast ramping, while still covering the full area desired to be heated. These panels run in parallel in the situation as shown in FIG. 8 (typically adjacent to one another) regardless of whether the power is coming from one or more batteries. In one example, the area of the conductive sheet was 11×15.5 in (170.5 In$^2$), it was desirable to have at least two heating panels adjacent to one another.

In some illustrative embodiments, the number of batteries 212, 216 may be minimized and could even be one in some embodiments. In order to use fewer batteries, it may be advantageous to add a charge pump to the circuit wherein a controller 200 applies power to the heating elements 132 from the charge pump for a ramp up time, and then switches the power application to a secondary circuit similar to that of FIG. 8. A charge pump increases a voltage, and a larger voltage means a larger current applied across the resistance. This may only be desired for a short period of time, and because readily available batteries are limited in some cases to 3.7V, if it is determined that 11.1V is desired initially but 7.4V is needed in steady state, the charge pump may boost the voltage temporarily to 11.1 across the heating element 128 to rapidly ramp the temperature, and then the controller 200 may switch the power to coming from the 7.4V battery source which may be duty cycle modulated. In this way the system 100 may only require 2 of the 3.7V batteries, while still being able to apply 11.1V for the short time needed.

Figure 11:
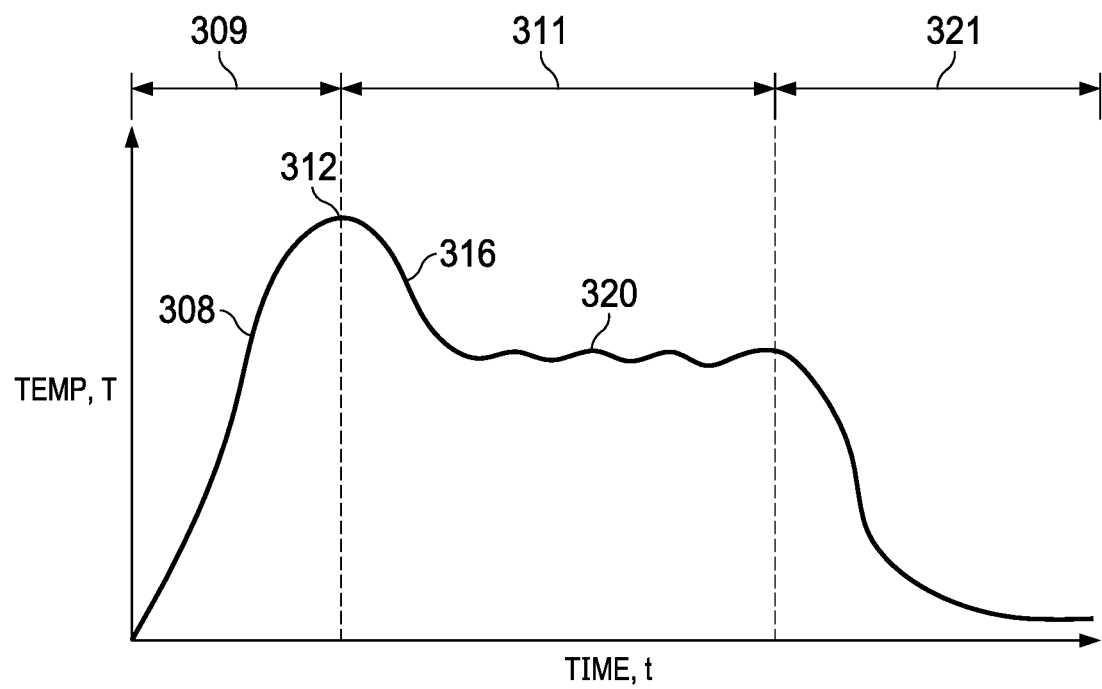
FIG. 11 is a graph presenting a qualitative, representative presentation of a temperature versus time profile for an illustrative recovery system.

In one illustrative embodiment, the control unit 164 increases the pressure (activates pump 160 until a desired pressure or predetermined maximum temperature is realized by pressure sensor 192) and then the temperature is ramped (See FIG. 11). This may be advantageous for extending the battery 196 life since the heat will be experienced more quickly with the pressure already applied because this brings the heating element 128 closer to the skin of the user.

Without being limited by theory, it is believed that the wavelength of the peak emissivity of the heating element reduces with increasing temperature (i.e., more power applied). This decrease in wavelength further means the less the deep into the tissue the radiation penetrates (i.e., it is nearer the skin surface). The nerves the perceive heat at near the skin surface so where a goal here is to stimulate those nerves to give a strong perceived heat, it means it is desirable to increase the power applied to the heating element. For this reason, more power may be applied at the outset. Moreover, with the system in many embodiments, the net heat is shifted towards conductive heat transfer with the user of specific heating element materials because of the material property phenomenon. In use, there is a shift in perception. It is acknowledged that at the higher power at the beginning is probably not safe for prolonged periods. Thus, timing or monitoring the temperature may be done to enhance safety.

Figure 9:
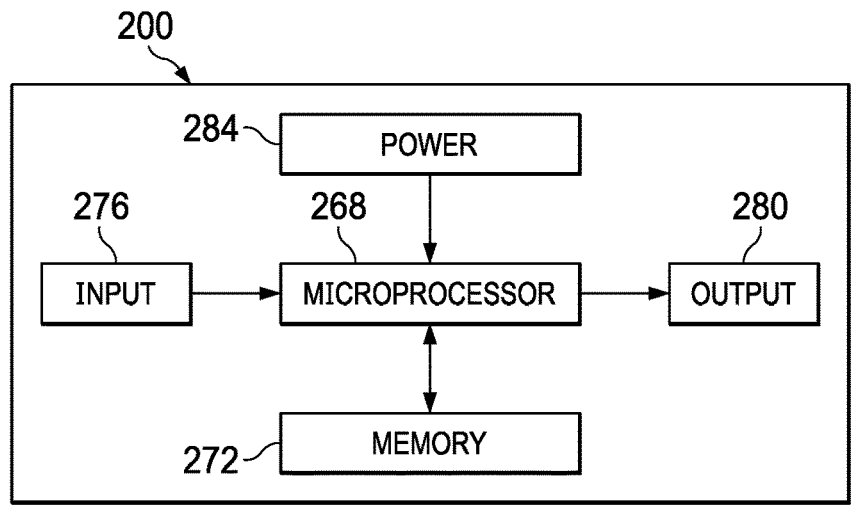
FIG. 9 is a schematic diagram of an illustrative controller for use as part of a recovery system.

Referring now primarily to FIG. 9, an illustrative embodiment of the controller 200 is presented. The controller 200 may be a programmable computer. A programmable computer is a machine that is, in general terms, typically comprised of at least memory for storing one or more programs of instructions and a processor, such as a central processing unit (CPU), for performing a sequence of arithmetical and logical operations based on the program instructions stored or otherwise read or received by the computer. The controller 200 includes at least one processor 268 such as, but not limited to, a microcontroller, microprocessor, or microcomputer. The processor 268 interacts with at least one non-transitory memory 272, or computer-readable media. The processor 268 receives input 276 and can have output 280. Power 284 is supplied to the controller 200 such as from the battery 196 (FIG. 5).

The non-transitory memory 272, or computer-readable media may take many forms. Any suitable computer usable or computer readable medium may be utilized. The computer readable medium may be a computer readable signal medium or a computer readable storage medium. The computer-usable, or computer-readable, storage medium (including a storage device associated with a computing device or client electronic device) may be, for example, but not limited to, an electronic, magnetic, optical, electromagnetic, infrared, or semiconductor system, apparatus, device, or any suitable combination of the foregoing. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a media such as those supporting the internet or an intranet, or a magnetic storage device. Note that the computer-usable or computer-readable medium could even be a suitable medium upon which the program or routine is stored, scanned, compiled, interpreted, or otherwise processed in a suitable manner, if necessary, and then stored in a computer memory. In the context of this document, a computer-usable or computer-readable, storage medium may be any tangible medium that can contain or store a program for use by or in connection with the instruction execution system, apparatus, or device.

The processor 268 may control any one of a radiating heating element 206, a conduction heating element 210 (FIGS. 6-7), the pump 160 (FIG. 5), the exhaust valve 184 (FIG. 5) or optionally other actuators or outputs, display 248 (FIG. 8), and may take input data from any number of sensors, such as but not limited to, a pressure sensor 192. The processor 268 may further connect to any secondary controllers or displays via wireless connection or wired connection. Such embodiments are not shown for the sake of brevity, but the reader should understand many such IoT systems exists for remotely collecting and displaying information and controlling devices.

The processor 268 and non-transitory memory 272 allow for various steps or methods to be programmed for the system 100. Some such methods or steps will be presented as examples further below. One aspect of the programs is to facilitate temperature control and examples of the same will now be given.

Figure 10:
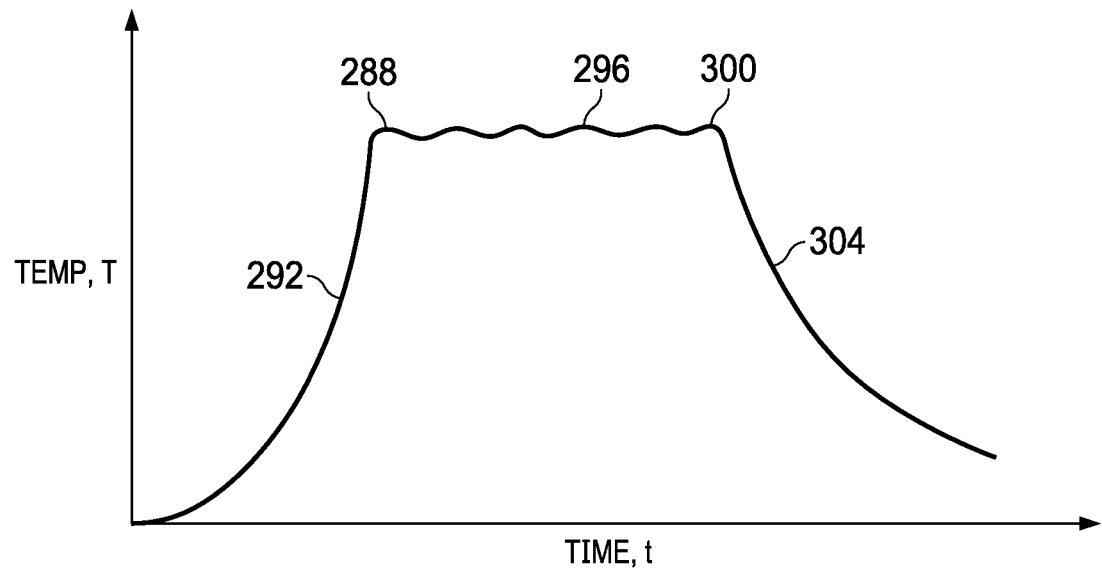
FIG. 10 is a graph presenting a qualitative, representative presentation of a temperature versus time profile for an illustrative recovery system.

In one illustrative embodiment, the controller 200 includes software or programming for use with the processor 268 that provides power to the heating elements 204, 208 with a desired temperature profile. For example, with reference to FIG. 10, an illustrative, qualitative temperature profile 288 includes a quick ramping portion 292 that leads to a treatment temperature 296 (or normal operation mode) before energy is terminated or reduced at energy adjustment point 300 allowing for a tapering of the temperature at segment 304. It should be understood that steeper or slower ramping portions 292 may be used. In some embodiments, the temperature may be cycled to have a tooth appearance or oscillation at the treatment temperature as shown. The controlled temperature profiles may have the advantage of cutting down on the time that the unit is worn and may enhance the user's perception of the product as it heats quickly. Moreover, an advantage may include a therapeutic benefit of quickly ramping the temperature.

In another illustrative embodiment, the temperature may be programmed to ramp 308 overshoot the treatment temperature as shown at 312 in FIG. 11 and ramp down 316 to the treatment temperature or target temperature 320 over a period of time. There is ramping period 309, treatment period 311 that starts with a ramp down, and a final ramp down period 321. The ramping period 309 shows a steep curve upward and to the right on the graph. As used here "steep" means have an effective overall angle between 30 and 89 degrees, and in some embodiments between 35 and 85 degrees. This ramping of the heat may have the perceptual advantage to the user 104 that the treatment is working without risking burning the user due to prolonged heat at an elevated temperature.

In another illustrative embodiment, the ramping of the pressure applied by the pneumatic subsystem 140 may be ramped or varied in a manner similar to that described for temperature in the preceding paragraphs. In still another illustrative embodiment, both temperature and pressure may be varied in patterned profiles, such as suggested in FIGS. 9-10.

In one illustrative embodiment, the controller 200 is formed using low-profile components or flexible circuits to allow the different electronic components to be a flexible, low-profile layer that may be attached to the flexible wrap 108. The controller 200 may thus be a sheet or layer that is attached with a hook-and-loop attachment to the flexible wrap 108. In that way, the controller 200 or control unit 164 remains low profile but may be removed for cleaning of the flexible wrap 108 or the controller 200 or control unit. This embodiment may also make it easier to for changing out components that fail. This embodiment may include batteries that are separately removable for charging or that may be charged in position. Moreover, the circuit patterns may be visible or even enhanced to glow in order to provide an iconic aesthetic on the outside of the user.

Figure 12:
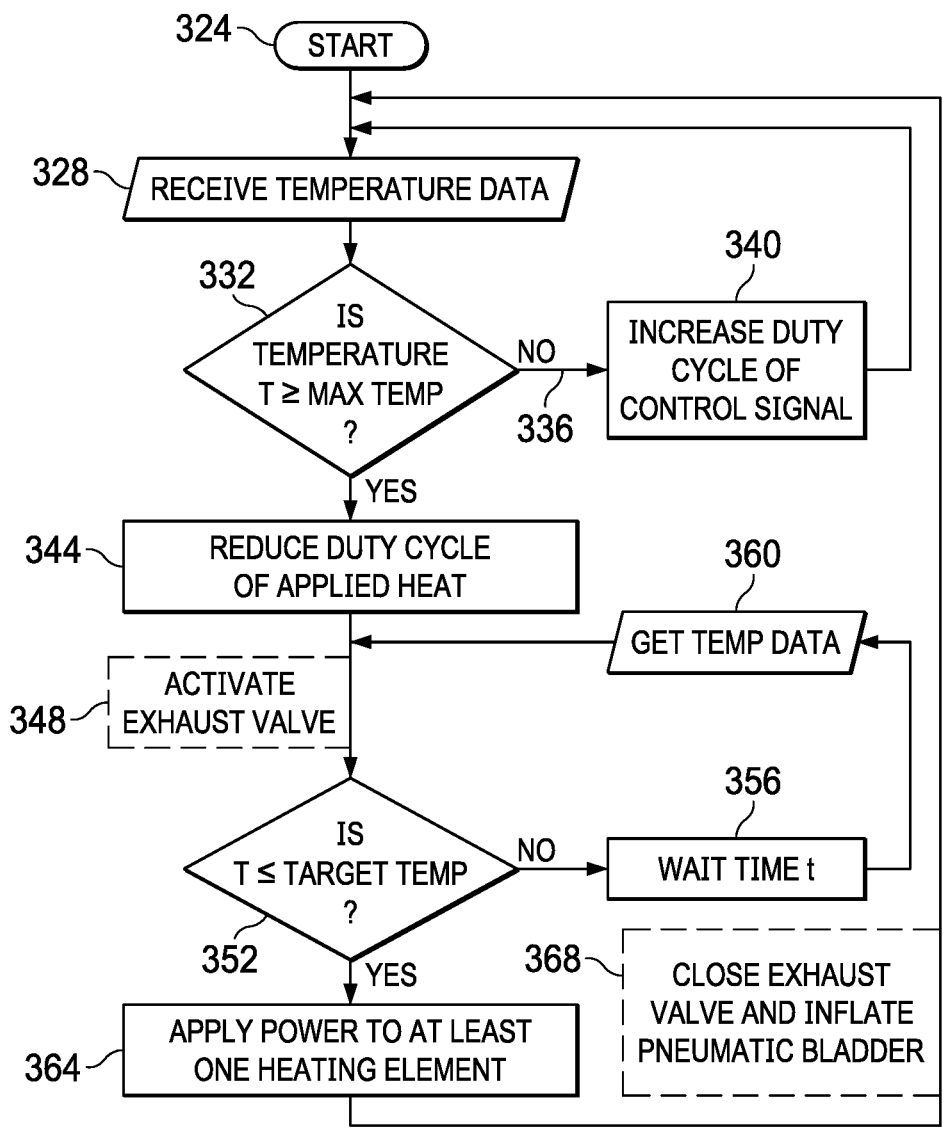
FIG. 12 is a process flow diagram for an illustrative temperature routine for an illustrative recovery system.

Referring now primarily to FIG. 12, an illustrative process flow for how the controller 200 and memory 272 may control temperature or utilize a temperature routine. The process begins at 324 and the controller 200 receives temperature data at 328 from one or more thermocouples 202 (FIG. 5). The controller 200 asks at interrogatory 332 if the temperature data received at 328 shows the temperature is greater than or equal to a max temp or a selected temperature. If it is no, the process continues on path 336 to a step of increasing the duty cycle of the control signal at 340, or in other words apply more heat. The process then proceeds back to 328 and again to interrogatory 332.

If the answer to interrogatory 332 is affirmative, the process continues to step 344 where the duty cycle is reduced, or in other words the heat applied is reduced. If the max temperature has been exceeded or reached, in one embodiment, the exhaust valve 184 (FIG. 5) is activated at step 348 to lower the pressure on the user and reduce the chance of burn or irritation. In some embodiments, this step is not done or is only done if the temperature data shows the max temperature has been exceeded by a certain margin, e.g., 10%. In some embodiments, if the temperature is too high—putting the user at risk of injury—the system can reduce the temperature, the pressure, or both. In one such embodiment, the pressure is reduced first. In some embodiments, the pressure is always maintained at a high level to minimize energy use from the batteries or battery.

After either reducing pressure or not, the process after step 344 continues to interrogatory 352 which asks if the temperature is less than the target temperature, or in some embodiments some percentage of the maximum temperature. In the present example, the interrogatory 352 asks if the temperature is less than or equally to 90% of the maximum temperature. If the answer to interrogatory 352 is negative, the controller 200 provides a timeout at step 356 of a time t before moving to step 360 to get the temperature again. The process then continues to interrogatory 352 again.

If the answer to interrogatory 352 is affirmative, the process continues to step 364, which applies power again to the at least one heating element 128. Because the temperature is in control, pneumatic pressure may again be applied in some embodiments as shown at step 368 and the process continues back to data input at 328. This is only one illustrative embodiment and those skilled in the art will understand that many other processes may be utilized.

Figure 13:
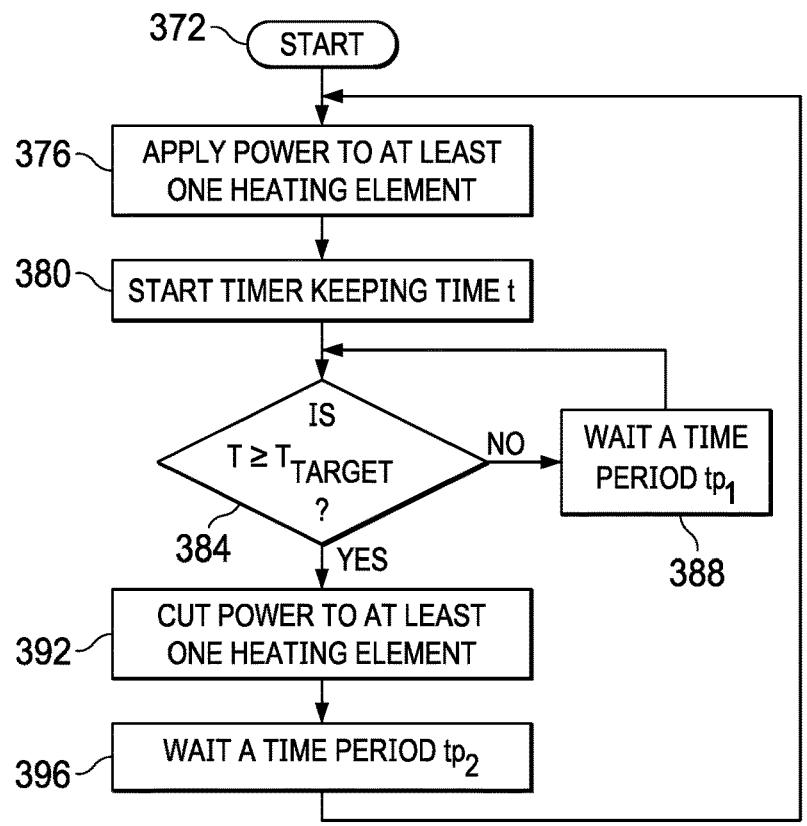
FIG. 13 is a process flow diagram for an illustrative temperature routine for an illustrative recovery system.

Referring now primarily to FIG. 13, another illustrative process flow for how the controller 200 and memory 272 may control temperature or utilize a temperature routine is presented. The process begins at 372 and goes to step 376 which has the controller 200 apply power to the at least one heating element 128 and starting a timer shown at 380. The process then asks at interrogatory 384 whether the temperature is greater than or equal to the maximum temperature, or in some embodiments a desired, selected temperature. If the answer to interrogatory 384 is negative, the process waits for a time period tp1 at step 388 before returning to interrogatory 384 again. If interrogatory 384 is answered in the affirmative, the process continues to step 392 which has the controller 200 cut the power to the at least one heating element 128 and wait another time period, e.g., tp2, at 396, before starting the process again. Again, this is just another illustrative embodiment and those skilled in the art will appreciate that many different processes may be used for control of the recovery system 100.

Figure 14:
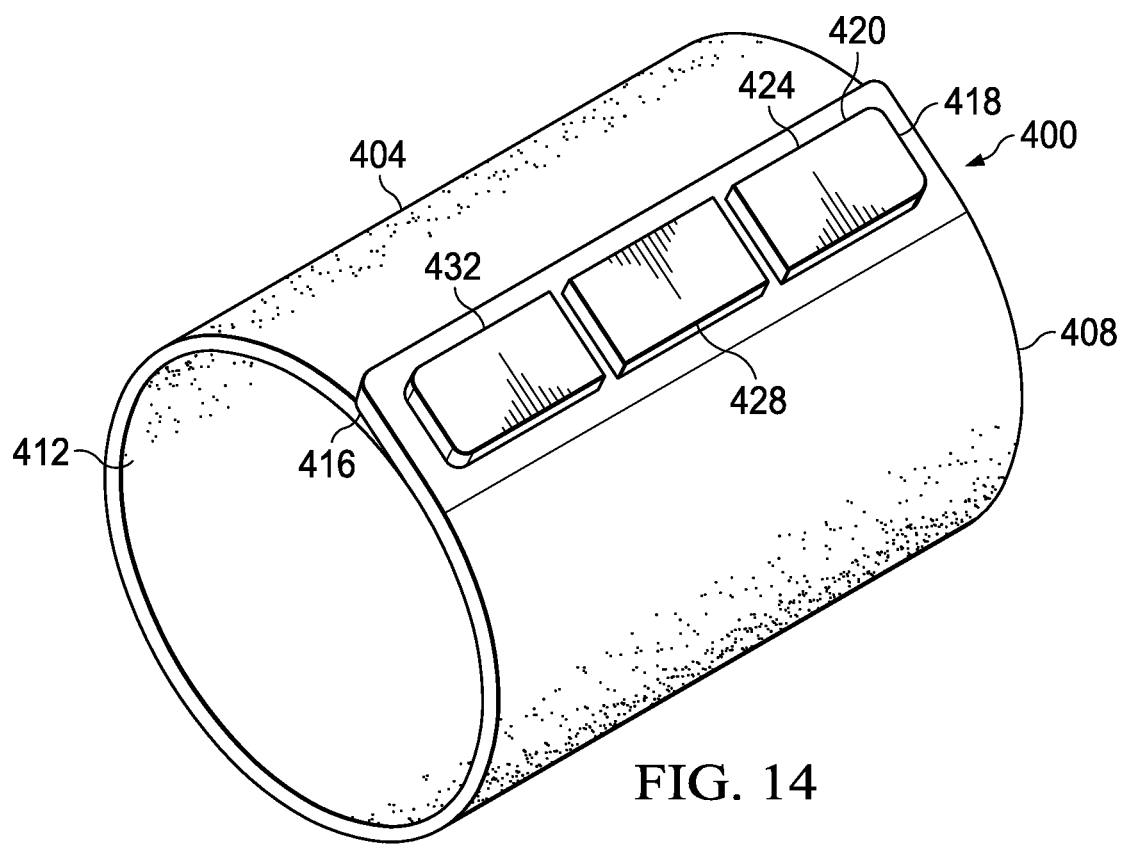
FIG. 14 is a schematic perspective view of an illustrative embodiment of a recovery system.
Figure 15:
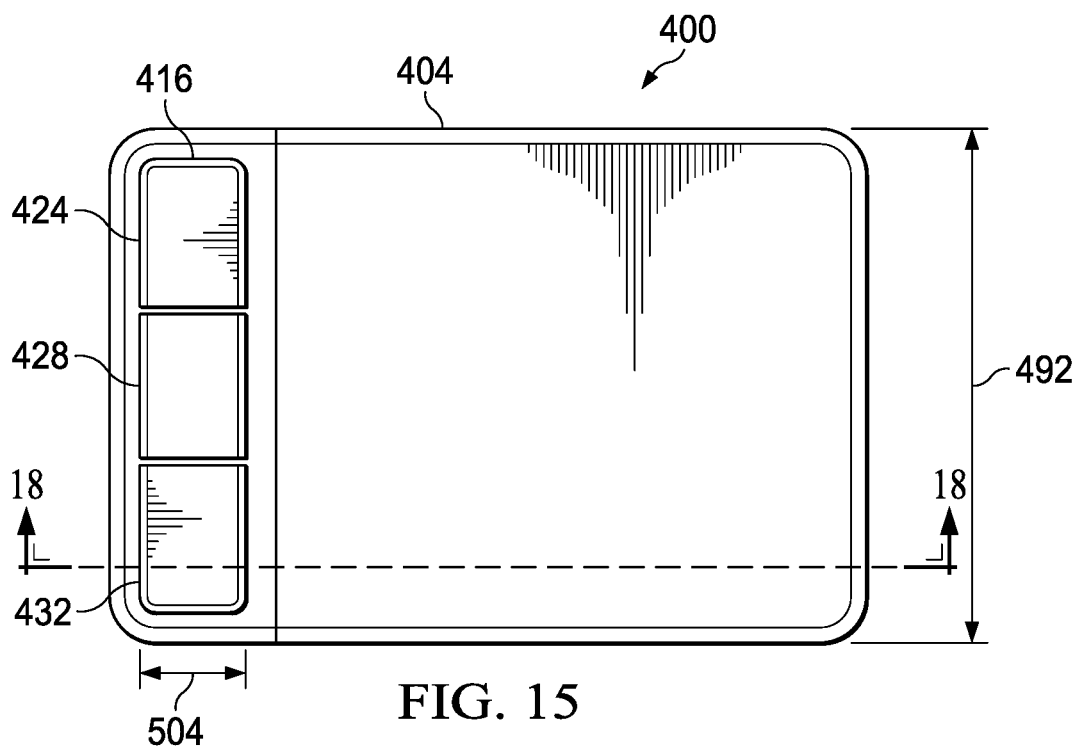
FIG. 15 is a schematic plan view of the illustrative embodiment of a recovery system of FIG. 14.

Referring now primarily to FIGS. 14-20, another illustrative embodiment of a portable, battery-powered recovery system 400 is presented. FIG. 14 shows the portable, battery-powered recovery system 400 in position that is curved to apply around a user's limb and FIG. 15 shows the portable, battery-powered recovery system 400 in plan view from the top. The portable, battery-powered recovery system 400 is analogous in many respects to the system 100 presented above.

The system 400 includes a flexible wrap 404 sized and configured to surround a portion of the user's body 104 (FIG. 1). The flexible wrap 404 has a first side 408 and a second side 412. The first side 408 is outward facing when in an applied position and the second side 412 is inward facing when in the applied position. The flexible wrap 404 has a flexible-wrap fastener 416 coupled to the flexible wrap 404 for releaseably securing the flexible wrap 404 around the portion of the user's body.

The system 400 includes at least one heating element (analogous to 128 above) coupled to the flexible wrap 404. A control unit 418 may include a plurality of sealed compartments 420, e.g., compartments 424, 428, 432. The compartments 420 may be formed with spaces or gaps 422 between them. The compartments 420 may hold one or more batteries 426 and or one or more printed circuit boards 430 (FIG. 20) for the controller unit and for push buttons (e.g., see 434).

Figure 16:
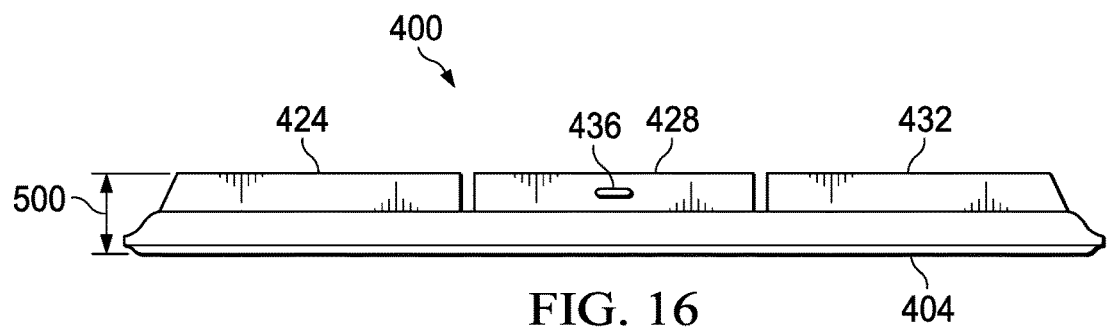
FIG. 16 is a schematic elevation end view of the illustrative embodiment of a recovery system of FIG. 14.

The system 400 may or may not include a pneumatic subsystem and controller analogous in most respects to that in previous embodiments. The system 400 holds the battery or batteries and the controller within the sealed compartments 420. The control unit may include an output and input device through a USB port 436 (FIG. 16). The battery or batteries may be recharged through charging port 440 (FIG. 17).

Figure 17:
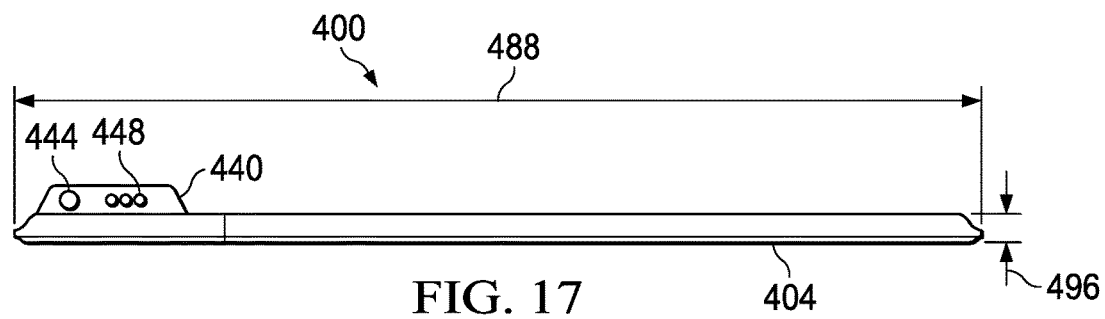
FIG. 17 is a schematic elevation side view of the illustrative embodiment of a recovery system of FIG. 14.

An on/off switch 444 and LED indicators 448 may be on one side of a compartment, e.g., compartment 432, as shown in FIG. 17. The LED indicators 448 may show the level of heat applied (e.g., high, medium, low) or may show battery level remaining, or both.

Figure 18:
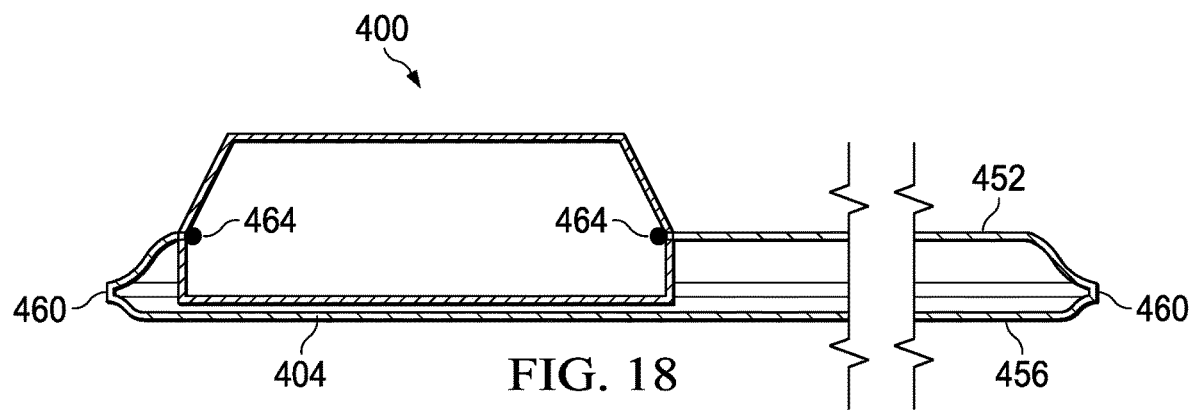
FIG. 18 is a schematic longitudinal cross section of the illustrative recovery system of FIG. 14 taken along line 18-18.

Referring primarily to FIG. 18, the flexible wrap 404 may have a top material or fabric 452 and a bottom material or fabric 456 with a welded edge 460 or other coupling along a perimeter. The electronics housing or compartments 420 may include a groove that receives a press fit edge 464 of the top material 452.

Figure 19:
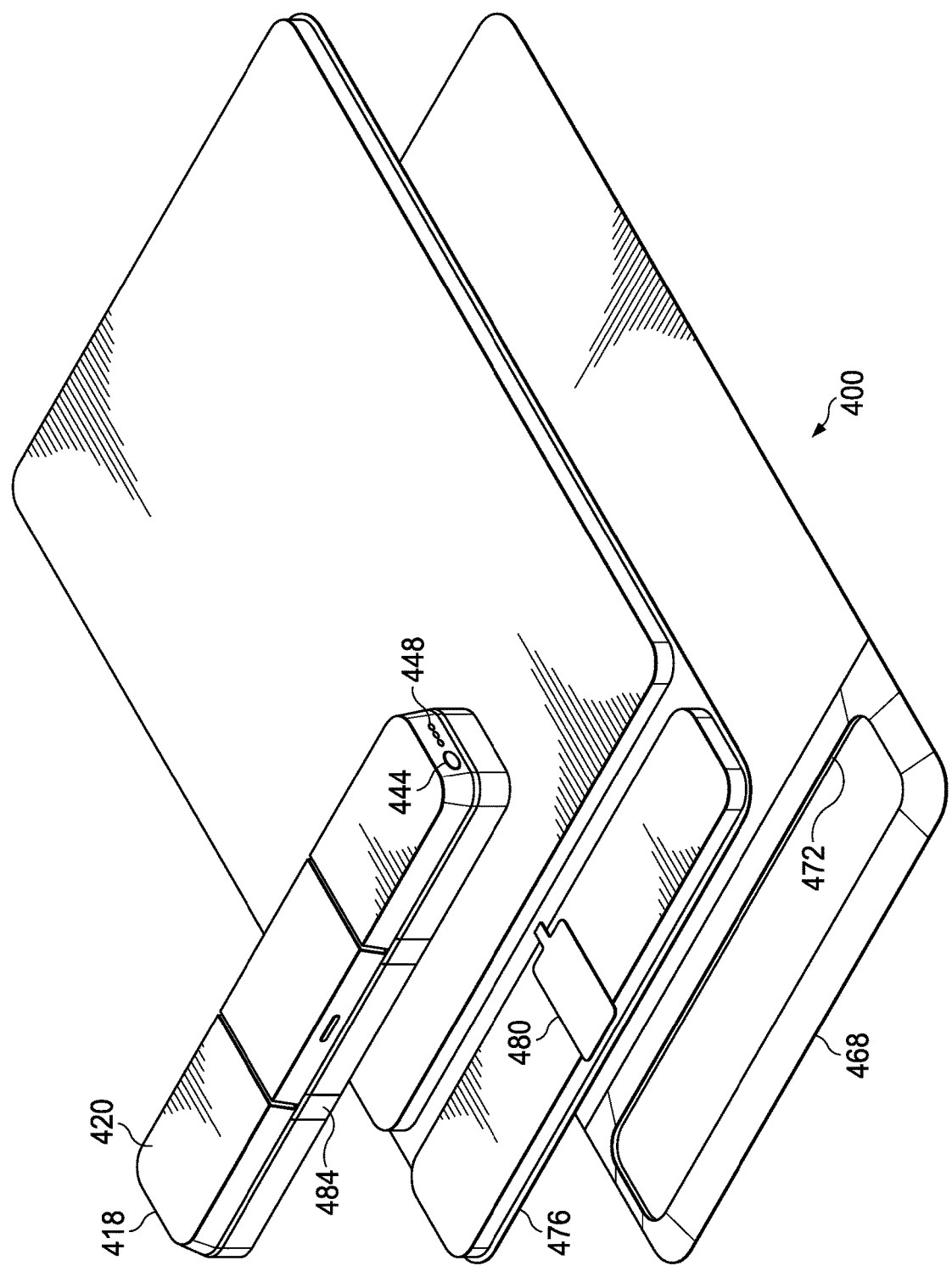
FIG. 19 is a schematic, partially disassembled perspective view of an illustrative embodiment of a recovery system.
Figure 20:
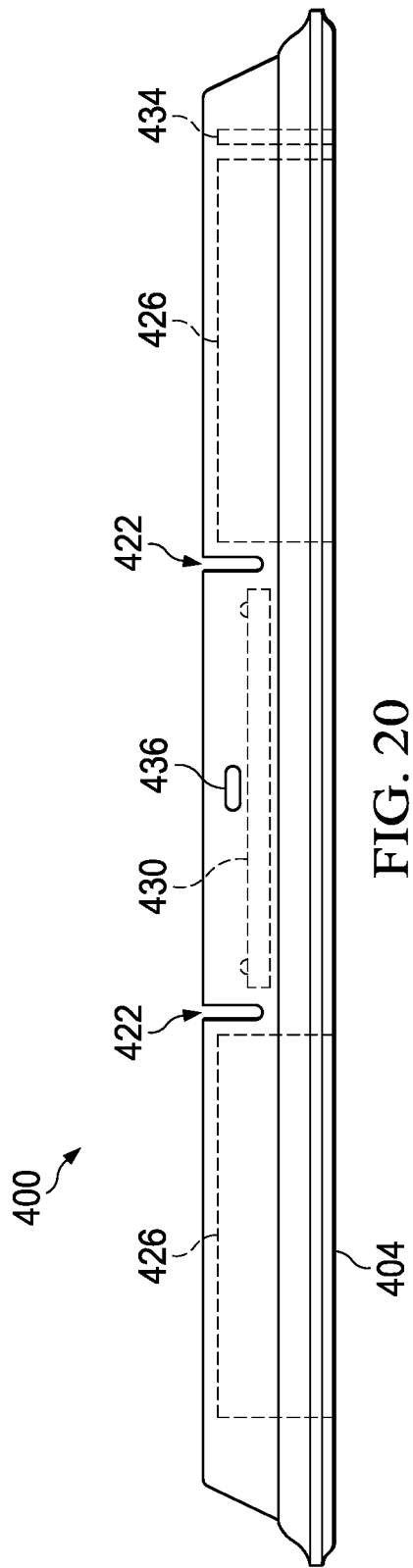
FIG. 20 is a schematic elevation end view of the illustrative embodiment of a recovery system.

In some illustrative embodiments, the layers going from the second side to the first side at some locations include a bottom polymer sheet for heat transfer, a heating element, an electronic connector for the heating element, a compartment with PCB or battery, and a top polymer. Referring now primarily to FIG. 19, various layers are visible. The bottom layer shown 468 is a sleeve that has an elastic section with a press fit edge 472 for sealing on to electronics. That layer is the fabric cover that can be cleaned. The next layer 476 shown is the internal components encased in an elastomer. The internal components include the at least one heating element and a coupling 480 for electrically coupling to the control unit 418. The final layer is the control unit 418, which has compartments 420. The gaps 422 (FIG. 20) may be filled to form flexible joints 484 between compartments.

Those skilled in the art will appreciate that the flexible wrap 404 may be sized for different applications and the recovery system 100, 400 may take numerous sizes and shapes for different applications. For example, the flexible wrap 108, 408 may be of any suitable geometry, size, and shape to provide sufficient heating and compression as discussed above. The flexible wrap 108, 408 and heating element assembly may come in multiple lengths and widths to accommodate a range of individuals, and not necessarily minimized in the number of variations, but rather targeted toward a specific range of limb girths, or user types, or joints to cover. It may be noted that wider garments may apply more compression and have potential additional benefits that do not require dynamic movements.

Referring again primarily to FIGS. 15-17, the dimensions of the flexible wrap 404 are referenced as follows: Longitudinal length 488 (FIG. 17), lateral length 492 (FIG. 15), and depth 496 (FIG. 17). The flexible wrap with compartment may have a depth 500 (FIG. 16) and the compartments a width of 504 (FIG. 15). In one illustrative embodiment, the longitudinal length 488 is 393.7 mm, lateral length 492 is 279.4 mm, depth 496 is 11 mm, layer, and compartment depth 500 is 24 mm, compartment width 504 is 63 mm.

Figure 21:
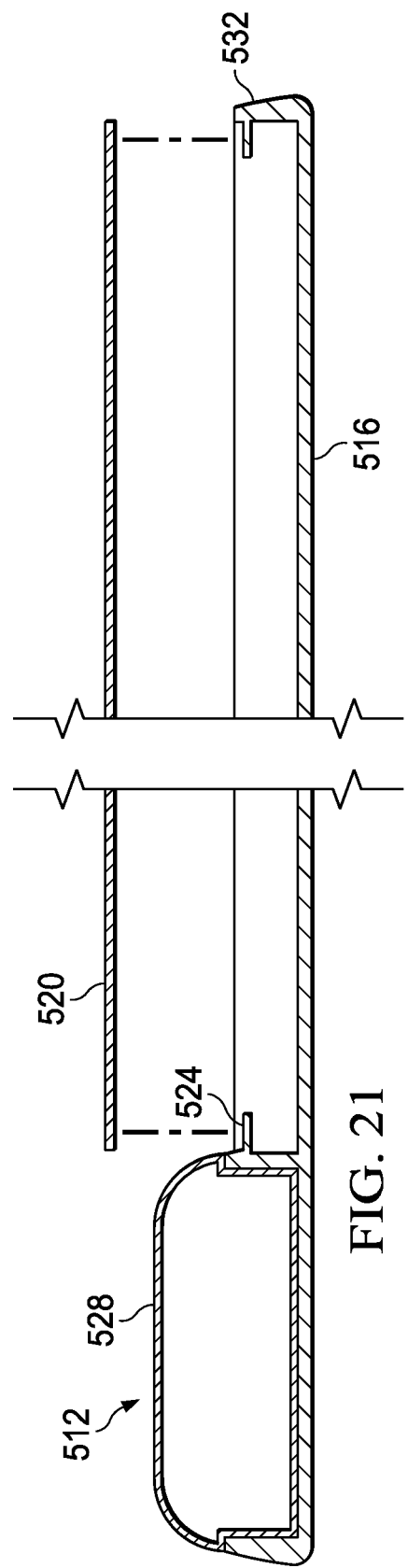
FIG. 21 is a schematic longitudinal cross section of an illustrative embodiment of a recovery system.

Referring now primarily to FIG. 21, another illustrative embodiment of a portable, battery-powered recovery system 512 is presented. The system 512 is analogous to the embodiment previously presented in most respects. This embodiment differs in that it is a molded construction. The system 512 has a molded elastomer exterior 516, a molded top 520, and welded overlaps 524 extending on one end from an electronics housing 528 and from a distal end 532 on the other.

Figure 22:
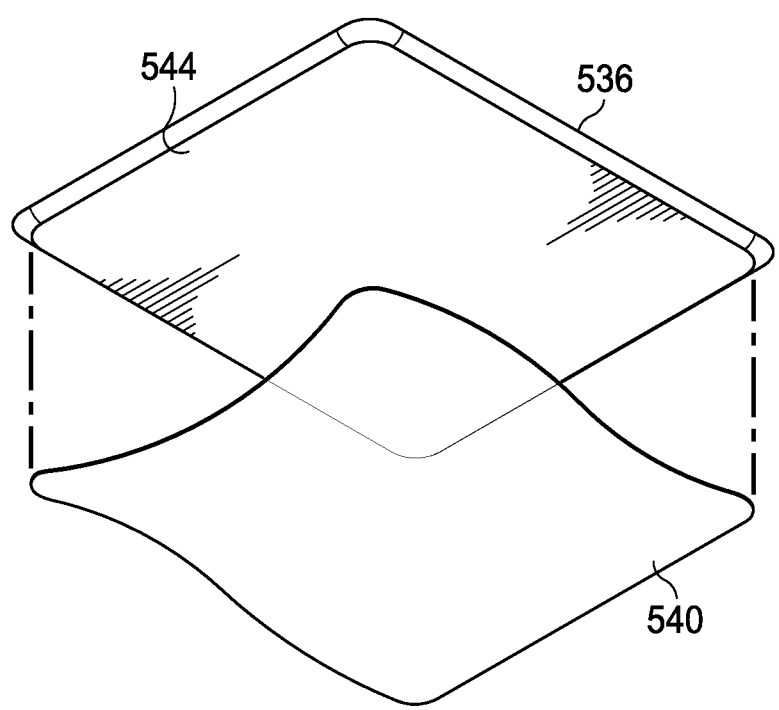
FIG. 22 is a schematic, partially disassembled perspective view of an illustrative embodiment of a recovery system.
Figure 23:
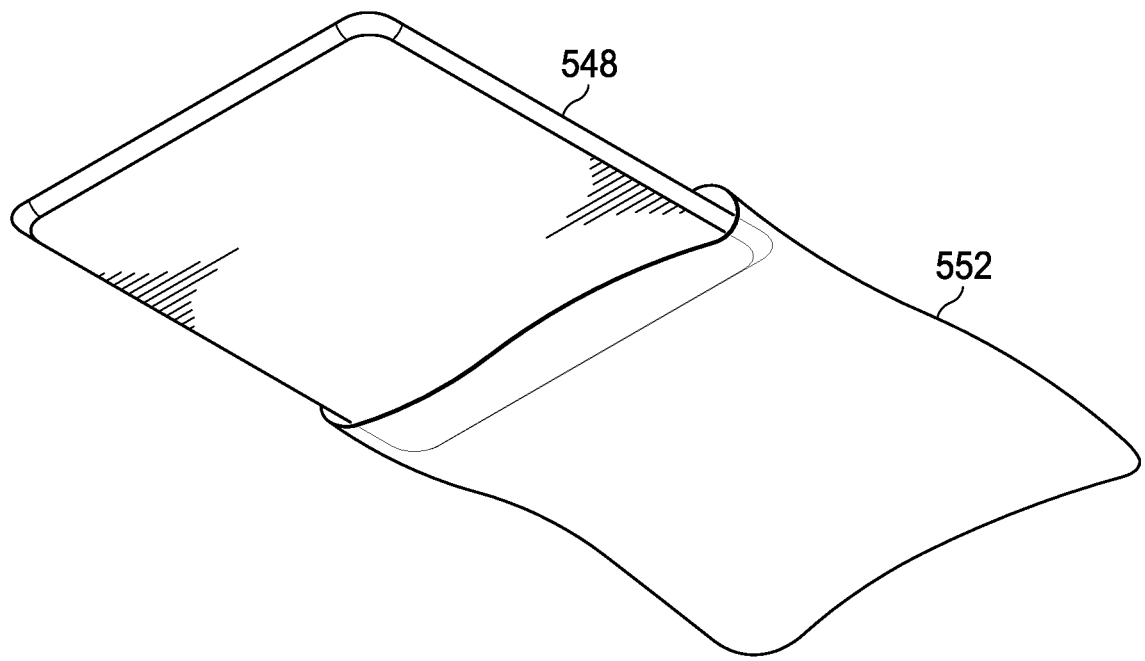
FIG. 23 is a schematic, partially disassembled perspective view of an illustrative embodiment of a recovery system.

It has already been referenced that it may be desirable to wash or sterilize portions of the portable, battery-powered recovery systems. FIGS. 22 and 23 present two more ways to do that. FIG. 22 shows a flexible wrap 536 has a self-sticking, non-adhesive fabric 540 that adheres to a second surface 544 of the flexible wrap 536. It may utilize micro-suction cups, static cling, or embedded magnets. The fabric 540 can be cleaned and repositioned between uses. The embodiment of FIG. 23 presents a flexible wrap 548 being inserted into a fabric bag or pouch 552. The bag or pouch 552 can be cleaned, sterilized, or replaced between uses.

In one illustrative embodiment, a sanitary liner may be removably attached to the inner surface of the flexible wrap or garment when in the deployed position. The liner may be disposable or may be removed for cleaning and re-used. The liner may be polyurethane coated fabric or a PVC coated fabric or the like.

Figure 24:
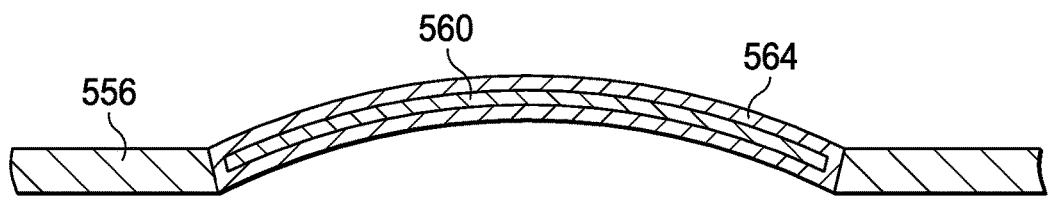
FIG. 24 is a schematic cross section of a flexible wrap of an illustrative recovery system showing an arcuate member for enhancing blood flood around the flexible wrap.

Referring now primarily to FIG. 24, a feature that may be included with the portable, battery-powered recovery systems is presented. In this embodiment, a layer 556 included in a flexible wrap has distributed within the layer 556 hard arcuate members 560, or blood-flow-channel members, that form blood flow channels 564. The blood flow channels 564 may provide for improved blood flow within the area of the channel when the flexible wrap is applied and particularly when pneumatic pressure is being applied. In one illustrative embodiment, the hard arcuate members 556 are shaped like half-moons and are hard enough to not deform so much as to stop or hinder the blood flow under them when applied.

If the flexible wrap 108, 408, 536, 548 extends around a limb to apply pressure thereto without more it might, in some circumstances, be overly restricting blood flow or acting as a tourniquet. The channel, which can be part of a plurality of blood flow channels, may be formed by using rigid, or semi-rigid spacers or arcuate members. In this embodiment, the arcuate members 560 are a hard plastic with a concave portion that faces the user. The blood can pass through those portions without the restriction that would otherwise exist.

The arcuate members 560 form blood flow channels that are orientated parallel with the long axis of the user's limb, as this is the direction of physiologic blood flow. In some embodiments, the arcuate members 560 are placed in the innermost portion of the wrap (closest to skin). In some embodiments, the arcuate members 560 are built into the pneumatic chambers. In the latter placement, the arcuate members 560 are effectively placed between chambers that run along a distal to proximal axis of the user's limb when applied.

Some embodiments may only have the heating aspect and not the pneumatic aspects. Other embodiments may have only the pneumatic aspects and not the heating aspects.

In operation, according to on illustrative embodiment, the recovery system 100 may be used in various ways and the steps mentioned here may be modified or ordered in other ways. In one illustrative embodiment, the use may be initiated by sterilizing the fabric or exterior of the flexible wrap 108. In the case the user desires to sterilize the recovery system 100, 400, the user either cleans the inner surface of the flexible wrap 108, 408, 536, 548 in case the wrap itself is sterilize-able or affixes the disposable sterilized inner layer or pouch/sleeve, e.g., 540 or 552 in FIGS. 22 and 23. Next, in the case the recovery system 100 has a removable heating element assembly 134, the user 104, inserts or attaches the recovery element to the flexible wrap 108. In the case the control unit 164 or controller 200 is removable from the heating element assembly 134, the user 104, may also attach control unit 164 or controller 200 at this time to the heating element assembly 134. This process completes the assembly of the recovery system 100 for one embodiment. Note, in the case that the recovery system 100 is battery powered, there may be charging stations (not shown) and batteries may be added or removed during the setup process.

The user 104 places the recovery system 100 on a portion of their body where they desire to apply heat. The user 104 may optionally use wrapping segments of the flexible wrap 108 to wrap around their body for a snug fit, or otherwise just lay the flexible wrap 108 on top of the surface to heat up and potentially use weighted elements (not shown) to apply some pressure.

The user 104 may choose a setting for heat on a display on the controller unit 164 or a default temperature may be programmed. There may be numerous heat settings, e.g., three heat settings for low, medium, and high. In some embodiments, the control unit 164 may allow for many different temperature ranges with different display readouts. For example, the readout may be in the form of color only, a bar graph, digital readout, or a row of LED indicators (e.g., 448, FIG. 19). The controller 200 then controls the temperature of the one or more conduction heating elements 210 or radiating heating elements 206 to match the settings of the user 104. A negative feedback control loop may be used along with limit switches, e.g., a thermal fuse; these may be included to limit the amount of heat generated and prevent burning or irritation of the user's skin. Other temperature routines may be used as previously presented and as others skilled in the art will appreciate. Temperature limiting may be used with some embodiments.

As the heat is being applied, if the recovery system 100 includes a pneumatic compression bladder 144, the user 104 may similarly control the pneumatic compression with the control unit 164. The compression levels may have different settings, e.g., low, medium, and high, or otherwise a more gradual scale analogous to the temperature control. A display may incorporate other settings such as a time limit which may be similarly selected and displayed to the user. The compression may be modifiable by the user continuously during use, may automatically cycle between two or more preset values, or may maintain a static single value until the device is turned off or a time limit is reached.

The user 104 may adjust settings during the heating process to alter to the amount of heating or compression applied to their body.

When the user 104 is done with the recovery session or the timer expires, the controller 200 will turn off the one or more conduction heating element 210 or radiating heating element 206 and will exhaust any pneumatic bladder using the exhaust valve 184 if such elements were utilized. The user 104 then may undo the fasteners 116 on the flexible wrap 108, if utilized, and remove the recovery system 100 from their body.

As illustrated, there are many constructional permutations and combinations, and altering of various material properties which yield satisfactory results in an inflatable belt for use in a blood flow restriction system, and all such combinations and permutations and material property choices may be considered within the scope of this invention.

One skilled in the art will recognize that many of the components described may be combined into a single object via different manufacturing processes such as welding, injection molding, casting, etc. It may be recognized that many components in the system and their connection points, or connection means, may also be interchanged or rearranged to achieve the same effect as the disclosed configurations. For example, where it is discussed that it may be advantageous to de-couple the heating element assembly 134 from the flexible wrap 108, the equivalent construction may be obtained by for example, sewing an enclosure containing one of a conduction heating elements 210 or a radiating heating element 206 directly to the flexible wrap 108 and reducing the complexity of the system 100.

Further, where the figures show a single heating element assembly in communication with a garment 106, the garment may alternative have several distinct and separate heating element assemblies in communication with the garment and each separate heating element assembly may be controlled by a single controller or alternatively by multiple separate controllers. Such a system may have the advantage of varying the heating on different adjacent portions of the user's body.

In general, valves, and valve types, fasteners, such as cam locks, hook and loop fasteners, ratchet mechanisms, heat transfer elements etc. may be interchanged, used in quantities of more than one, altered in width, length, or profile, and the inventions disclosed herein may be considered to have encompassed all such permutations and combinations of such components.

Yet another example is the at least one pneumatic bladder 144 may have two input ports, one to allow air in and another in communication with an outlet system such as a pressure relief valve. While such design is not featured above, the reader may note this concept is another example of how multiple items may be employed, and components shifted within the system to connect with different components, while the same overall system and effectiveness are maintained. Further still, the location and placement of various elements may be moved and altered such that they appear to differ from the figures shown, and description attached, however, all such configurations and combinations may be considered within the scope of the disclosure herein.

In one illustrative embodiment, the garment and heating element assembly 101 are configured to provide 360 degrees heating to a user's limb. The garment 106 may be a wrap and the heating element is substantially coextensive with at least the portion of garment that touches the user during operation. Moreover, the pressure of the garment all the way around with heating may enhance the perception of useful treatment by the user. This may be particularly useful when the heating means involves IR.

With reference to the figures generally, in one illustrative embodiment, a portable, battery-powered recovery system 100 for a user includes a flexible wrap 108, 404, 536 sized and configured to surround at least a portion of the user's body to which a heating application is desired. The flexible wrap has a first side 120 and a second side 124. The first side 120 is outward facing when in an applied position and the second side 124 is inward facing when in the applied position. The system 100 also includes at least one heating element 128 coupled to the flexible wrap 108; a control unit 164 coupled to the flexible wrap and communicatively coupled to the at least one heating element for controlling the application of heat by the at least one heating element; and a battery 196 coupled to the flexible wrap and electrically coupled to the at least one heating element. The control unit comprises at least one processor and at least one non-transitory memory as those skilled in the art know well. The at least one non-transitory memory comprises stored instructions, which when executed by the one or more processors, causes the controller to (i.e., is programmed): to activate the at least one heating element to provide primarily conductive heat perceived by the user, and to activate the at least one heating element to provide primarily infrared radiation heat.

In another analogous embodiment, the at least one non-transitory memory includes stored instructions, which when executed by the one or more processors, causes the controller to: ramp power to the at least one heating element to provide primarily conductive heat perceived by the user, and decrease power to the at least one heating element to provide primarily infrared radiation heat. The ramping may according to the patterns presented in FIGS. 10-11. In another more detailed embodiment, the at least one non-transitory memory comprises stored instructions, which when executed by the one or more processors, causes the controller to: ramp power to the at least one heating element to provide primarily conductive heat perceived by the user; decrease power to the at least one heating element to provide primarily infrared radiation heat; and wherein the ramp of power is at least X % greater than normal operating power and X % may 20%, 30%, 40%, 50%, 60% or 70% or anything between 20-70%. In another illustrative embodiment, the temperature ramp occurs for between 30 and 120 seconds, e.g., 30, 40, 50, 60, 70, 80, 90, 100, 110, 120 second or anything between 30-120 seconds. Those skilled in the art will appreciate that other ramping times may be used. In one illustrative embodiment, that causes the temperature of the wrap to be between 100 and 160 degrees Fahrenheit.

Figure 25:
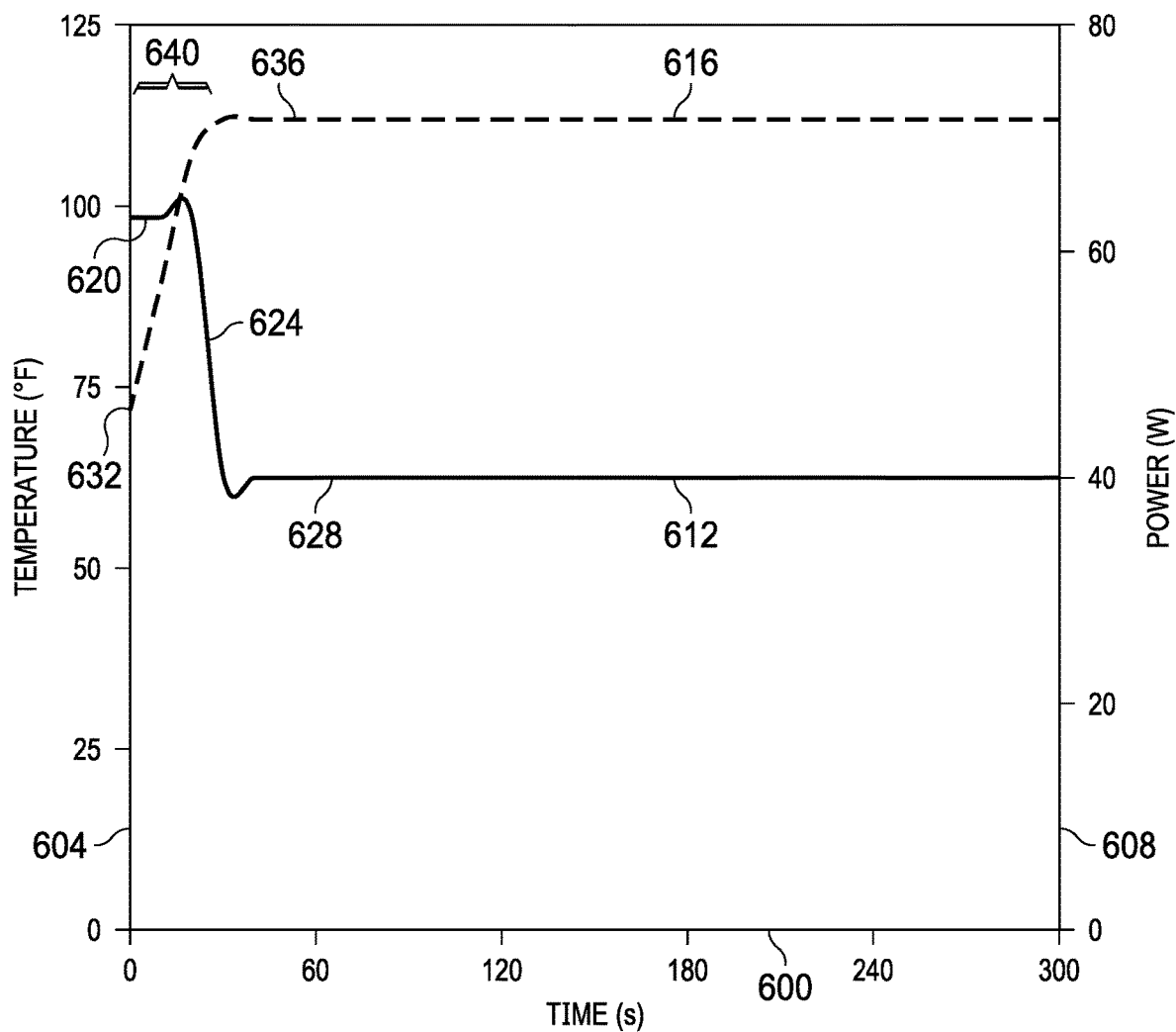
FIG. 25 is a schematic graph of theoretical data for a modeled portable, battery-powered recovery system (such as system 100 in FIG. 3 or 400 in FIG. 14) that includes a flexible wrap for securing an at least one heating element and presented with temperature and power on the ordinate axes and time on the abscissa axis.

Referring now primarily to FIG. 25, theoretical data is presented for an illustrative modeled portable, battery-powered recovery system (such as system 100 in FIG. 3 or 400 in FIG. 14) that includes a flexible wrap 108, 404, 536 for securing an at least one heating element, e.g., 128 (FIGS. 4-8), as previously presented. The modeling was done using the material properties of the constituent components. The temperature ramp was modeled based on testing evaluating temperature versus time performance relative to the amount of power applied. The initial temperature ramp was modeled after the time to therapeutic temperature, in this example 112 F, for the flexible wrap while at full power. As shown, an abscissa axis 600 (or X-axis) shows time represented in seconds (0-300 seconds). A left ordinate axis (Y-axis) 604 shows temperature in degrees Fahrenheit (0-125 F), and a right ordinate axis 608 is power in watts (0 to 80.00). A first trace 612 shows the power applied to the at least one heating element. A second trace 616 is the temperature over time. The temperature is measured at the surface of the wrap of the portable, battery-powered recovery system on the user/patient-facing side.

One can see that the power is initially placed in a high position as suggested by reference numeral 620, and then is decreased over segment 624 before being stabilized at a treatment setting 628. Meanwhile the temperature trace 616 goes from at or near ambient at 632 to a treatment temperature 636. Segment 640 is a ramping segment.

Figure 26:
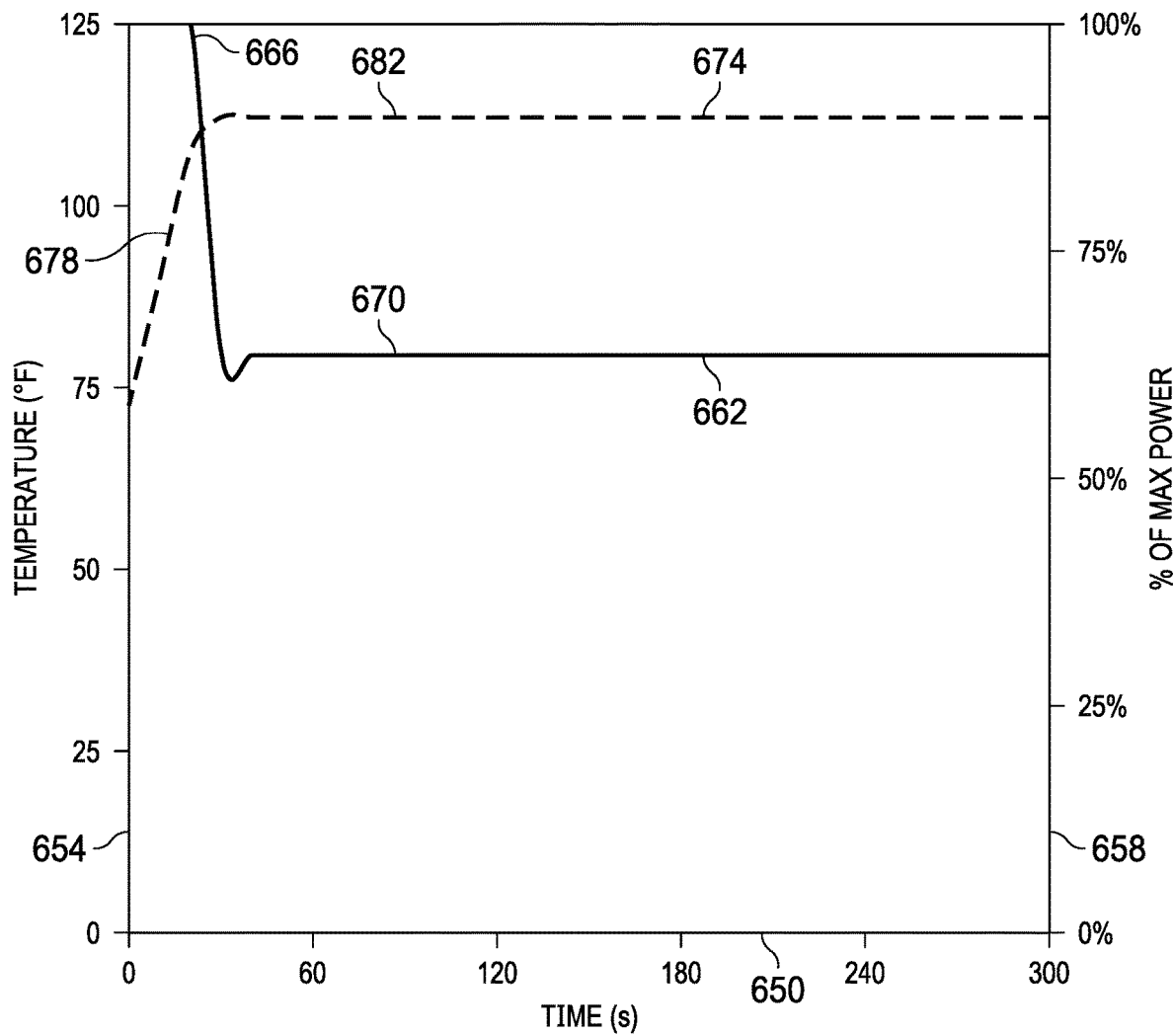
FIG. 26 is a schematic graph of theoretical data for a modeled portable, battery-powered recovery system (such as system 100 in FIG. 3 or 400 in FIG. 14) that includes a flexible wrap for securing an at least one heating element and presented with temperature and % max power on the ordinate axes and time on the abscissa axis.

In this illustrative embodiment, the temperature increases rapidly to 112° F. or higher on the wrap with the at least one heating element, as a result of the 63 Watts of power (or other amount) being applied. Once the desired therapeutic temperature is achieved, in this example 112° F., the power decreases to a level that is capable of maintaining the desired temperature. The change in power is illustrated on the graph at an approximate time 24 seconds, where the power decreases from 63 Watts to 40 Watts. In this example, the slope of trace 616 in the ramping segment 640 is approximately 1.66° F./S (or Fahrenheit/Second). The slope may be varied for some embodiments between 1.2 and 2.5° F./S or other ranges (Cf. FIG. 26). Other slopes are possible, and in some embodiments, the ramp segment is more exponential than linear. In addition, the desired or target therapeutic temperature can change based on the user's input, but the power ramp profile will remain approximately the same. The temperature ramp (or ramp segment 640) is to ensure the wrap, or pad, gets to the desired temperature quickly—often as fast as reasonably possible—given the capability and limits of the power supply.

Referring now primarily to FIG. 26, the same theoretical modeling as referenced in FIG. 25 is used to present a graph for a wrap with at least one heating element of a portable, battery-powered recovery system (such as system 100 in FIG. 3 or 400 in FIG. 14), although with different measurements, in part, shown than FIG. 25. In this graph, the abscissa axis 650 (or X-axis) is again time in seconds (0-300). The left ordinate axis 654 again presents temperature in Fahrenheit, but in this instance the right ordinate axis 658 presents percent of maximum power. A first trace, or power trace, 662 shows an approximation of the power starting at full capacity proximate numeral 666 and being decreased as the temperature rises to an operating level or treatment level 670 of about 62.5% in this illustrative embodiment. Meanwhile, the temperature trace 674 remains analogous to that shown in FIG. 25 and has a ramping segment 678 and a treatment portion 682.

Figure 27:
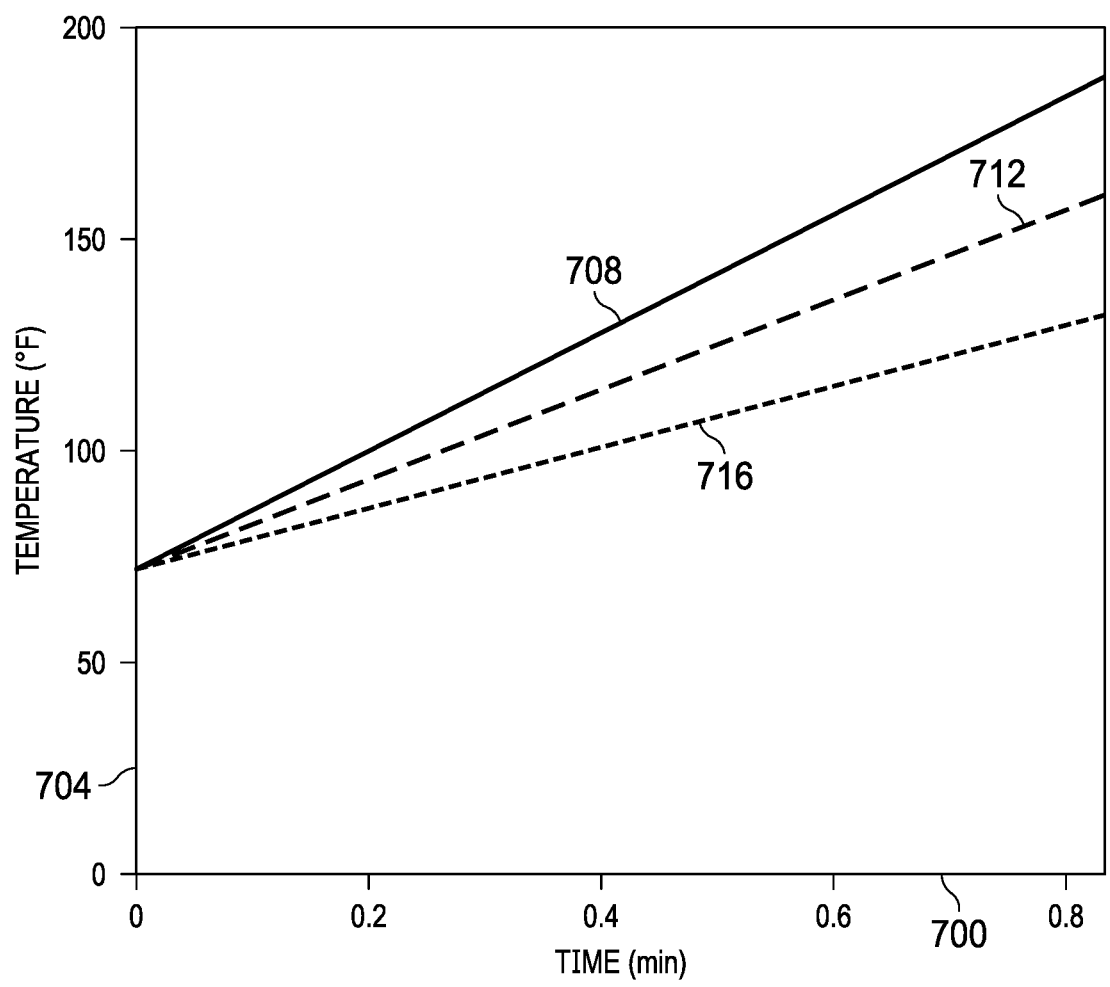
FIG. 27 is a schematic graph of theoretical data for a modeled portable, battery-powered recovery system (such as system 100 in FIG. 3 or 400 in FIG. 14) that includes a flexible wrap for securing an at least one heating element and shown with temperature on the ordinate axis and time on the abscissa axis for the temperature ramping segment.

Referring now primarily to FIG. 27, a temperature ramp range for theoretical embodiments of an illustrative wrap with at least one heating element of the portable, battery-powered recovery system (such as system 100 in FIG. 3 or 400 in FIG. 14) is presented. It presents the ramp in the ramping segment 640 (FIG. 25). The abscissa axis 700 represents time in minutes. The ordinate axis 704 is temperature in Fahrenheit. A first trace 708 is for a power setting of 69.3 Watts. This is based on a max power of approximately 63 W (+/−10%). A second trace 712 is for a power setting of 63 Watts. This is for a max power of approximately 69.3 W +/−10%. A third trace 716 is for a power setting of 56.7 Watts. This is based on a max power of approximately 56.7 W +/−10%. Reference 712 represents the max power of 63 W for this embodiment. Reference 708 represents max power +10% power or 69.3, whereas 716 represents max power −10% or 56.7 W.

Slope values for the traces 708, 712, 716 are based on an ambient temperature of 72° F. The slope equations are $T=72.0*x+72.0$ for trace 716 for power −10% of max power, $T=106.0*x+72.0$ for trace 712 for max power, and $T=140.0*x+72.0$ for trace 708 for max power plus 10%. The variable x represents time in minutes. These may be restated as the following slopes: 1.2° F./S (or Fahrenheit/Second), 1.76° F./S, 2.33° F./S, for traces 716, 712, 708, respectively. Again, the data for FIGS. 25-26 is based on modeling using material property data. Actual data for one embodiment is shown in the following figure. In one illustrative embodiment, the temperature ramp rate is 0.833° F./S. In another illustrative embodiment, the temperature ramp rate is in the range of 0.7° F./S to 2.8° F./S. Other ranges may be used or particular set points within any of the given ranges.

Referring now primarily to FIG. 28, actual data is presented for wrap with at least one heating element of the portable, battery-powered recovery system (such as system 100 in FIG. 3 or 400 in FIG. 14). The abscissa axis 720 presents time in seconds. The ordinate axis 724 presents temperature in Fahrenheit. The trace 728 is for the average thermocouple temperature. Trace 734 is for the FLIR average. Trace 738 is for the EXO2. Power was applied instantaneously at time 0, at which point the 14.8V was applied to the external wrap. Temperature stability during this testing was not evaluated. The data collection window was arbitrarily selected as 300 s or 5 min in this illustrative case.

As should be clear, there are many illustrative embodiments. A few examples follow.

Example 1. A recovery system for use by a user to address the user's muscles, the recovery system comprising:
a radiating heating element or a conduction heating element; and
a garment for securing the radiating heating element and the conduction heating element to a user; and
a battery coupled to the radiating heating element or a conduction heating element.

Example 2. The recovery system of Example 1, wherein the orientation of the radiating and conduction heating element are parallel to one another.

Example 3. The recovery system of Example 1, wherein the radiating and conduction heating element are further offset translationally from one another.

Example 4. The recovery system of Example 1, wherein the offset is at least 0.125 inches.

Example 5. The recovery system of Example 1, wherein the garment includes a plurality of wrapping segments for contouring to the user.

Example 6. The recovery system of Example 1, further comprising a controller and the controller regulating at least one of the radiating heating elements and the conduction heating element.

Example 7. The recovery system of Example 1, wherein the garment is separable from at least one of the radiating heating elements and the conduction heating element.

Example 8. The recovery system of Example 1, wherein the garment further includes a pneumatic compression element.

Example 9. The recovery system of Example 1, wherein the pneumatic compression element includes a plurality of inflatable chambers.

Example 10. The recovery system of Example 1, wherein at least two inflatable chambers are interconnected with an air pathway.

Example 11. The recovery system of Example 1, wherein the plurality of compression chambers is less than 4.

Example 12. The recovery system of Example 1, wherein the compression chamber dimensions are between 3 inches and 5 inches in width and the height is between 6 inches and 14 inches in height.

Example 13. The recovery system of Example 12, wherein the garment further includes a heating element attachment fastener for securing at least one of the radiating heating elements and the conducting heating element.

Example 14. The recovery system of Example 1, wherein the battery comprises a lithium-ion battery. Other examples can be given.

Although the present invention and its advantages have been disclosed in the context of certain illustrative, non-limiting embodiments, various changes, substitutions, permutations, and alterations can be made without departing from the scope of the invention as defined by the claims. It will be appreciated that any feature that is described in a connection to any one embodiment may also be applicable to any other embodiment.

What is claimed:

1. A portable, battery-powered recovery system for a user comprising:
   a flexible wrap sized and configured to surround at least a portion of the user's body to which a heating application is desired, the flexible wrap having a first side and a second side, wherein at least a portion of the first side is outward facing when in an applied position and at least a portion of the second side is inward facing when in the applied position;
   at least one heating element coupled to the flexible wrap;
   a control unit coupled to the flexible wrap and communicatively coupled to the at least one heating element for controlling the application of heat by the at least one heating element;
   a battery coupled to the flexible wrap and electrically coupled to the at least one heating element;
   wherein the control unit comprises at least one processor and at least one non-transitory memory; and
   wherein the at least one non-transitory memory comprises stored instructions, which when executed by the one or more processors, causes the controller to:
   to activate the at least one heating element to provide both conductive heating and radiation heat,
   and to provide an initial ramping segment in which a temperature increase caused by the at least one heating element is in a range of 0.75 to 2.5 Fahrenheit/Second until a desired treatment temperature is reached;
   and wherein the control unit is configured to vary the relative levels of conductive heat and radiant heat supplied to the user such that in a first mode of operation the at least one heater is configured to primarily provide conductive heat to the user and in a second mode operation the at least one heater is configured to primarily provide radiant heat to the user.

2. The recovery system of claim 1, wherein the at least one non-transitory memory comprises stored instructions, which when executed by the one or more processors, causes the controller to:
   ramp power to the at least one heating element to provide primarily conductive heat perceived by the user, and
   thereafter decrease power to the at least one heating element to maintain the desired treatment temperature while providing radiation heat.

3. The recovery system of claim 1, wherein the at least one non-transitory memory comprises stored instructions, which when executed by the one or more processors, causes the controller to:
   ramp power to the at least one heating element to provide primarily conductive heat perceived by the user;
   decrease power to the at least one heating element to provide primarily perceivable infrared radiation heat.

4. The recovery system of claim 1, wherein the at least one non-transitory memory comprises stored instructions, which when executed by the one or more processors, causes the controller to:
   ramp power to the at least one heating element to provide primarily conductive heat perceived by the user; and
   wherein the ramp of power is at least 40% greater than normal operating power.

5. The recovery system of claim 1, wherein the at least one non-transitory memory comprises stored instructions, which when executed by the one or more processors, causes the controller to:
   ramp power to the at least one heating element to provide primarily conductive heat perceived by the user; and
   wherein the ramp of power is at least 50% greater than normal operating power.

6. The recovery system of claim 1, wherein the at least one processor and the at least one non-transitory memory are programmed to apply power to the at least one heating element with a heat-application pattern on a temperature versus time graph, and wherein the heat-application pattern comprises an upward ramping portion, followed by a plateaued application portion, and followed by a termination decline portion.

7. The recovery system of claim 1, wherein the at least one heating element comprises at least one conductive heat element and at least one radiating heating element in the far infra-red range.

8. The recovery system of claim 1, wherein the at least one non-transitory memory comprises stored instructions, which when executed by the one or more processors, causes the controller to:
   ramp power to the at least one heating element for a duration between 20 and 120 seconds during which primarily perceivable conductive heat is provided, and
   thereafter decrease power to the at least one heating element.

9. The recovery system of claim 1, wherein the at least one non-transitory memory comprises stored instructions, which when executed by the one or more processors, causes the controller to:
   ramp power to the at least one heating element for a duration between 20 and 120 seconds to provide primarily conductive heat perceived by the user that provides a temperature between 100- and 160-degrees Fahrenheit, and decrease power to the at least one heating element to provide primarily perceivable infrared radiation heat.

10. The recovery system of claim 1, wherein the at least one heating element comprises a conductive sheet that comprises a rubber sheet formed with conductive particles.

11. The recovery system of claim 1, further comprising an outer flexible sleeve that encompasses the flexible wrap, and wherein the outer flexible sleeve is of a sterilizable material.

12. The recovery system of claim 1, further comprising blood-flow-channel members coupled to the second side of the flexible wrap to isolate a portion of the user's body from pressure applied to the user under the flexible wrap.

13. The recovery system of claim 1, further comprising:
a pneumatic subsystem comprising:
at least one pneumatic bladder coupled to the flexible wrap, and
a pneumatic pump coupled to the flexible wrap and fluidly coupled to the at least one pneumatic bladder, the pneumatic pump for selectively providing positive pressure to the at least one pneumatic bladder;
the control unit communicatively coupled to the pneumatic subsystem for controlling inflation of the at least one pneumatic bladder; and
wherein the battery is electrically coupled to the pneumatic subsystem.

14. The recovery system of claim 1, further comprising:
a pneumatic subsystem comprising:
at least one pneumatic bladder coupled to the flexible wrap, and
a pneumatic pump coupled to the flexible wrap and fluidly coupled to the at least one pneumatic bladder, the pneumatic pump for selectively providing positive pressure to the at least one pneumatic bladder;
the control unit communicatively coupled to the pneumatic subsystem for controlling inflation of the at least one pneumatic bladder;
wherein the battery is electrically coupled to the pneumatic subsystem; and
wherein the pneumatic subsystem further comprises one or more fluid conduits coupled to the pneumatic bladder and the pneumatic pump, and one or more pneumatic valves associated with the fluid conduits for controlling fluid flow therein.

15. The recovery system of claim 1, further comprising:
a pneumatic subsystem comprising:
at least one pneumatic bladder coupled to the flexible wrap, and
a pneumatic pump coupled to the flexible wrap and fluidly coupled to the at least one pneumatic bladder, the pneumatic pump for selectively providing positive pressure to the at least one pneumatic bladder;
the control unit communicatively coupled to the pneumatic subsystem for controlling inflation of the at least one pneumatic bladder;
wherein the battery is electrically coupled to the pneumatic subsystem;
wherein the pneumatic subsystem further comprises one or more fluid conduits coupled to the pneumatic bladder and the pneumatic pump, and one or more pneumatic valves associated with the fluid conduits for controlling fluid flow therein;
a flexible-wrap fastener coupled to the flexible wrap for releaseably securing the flexible wrap around the portion of the user's body;

wherein the pneumatic subsystem further comprises:
one or more fluid conduits coupled to the pneumatic bladder and the pneumatic pump, and
one or more pneumatic valves associated with the fluid conduits for controlling fluid flow therein;
wherein the at least one heating element comprises a rubber conductive sheet formed with rubber and conductive particles;
a plurality of heat sensors coupled to the flexible wrap and proximate to the user when in an applied position, and wherein the plurality of heat sensors is positioned to advance the heat sensors before other aspects of the heat wrap vis-à-vis the user;
wherein the at least one heating element comprises a conductive sheet;
a plurality of blood-flow-channel members coupled to the second side of the flexible wrap to isolate a portion of the user's body from pressure applied to the user under the flexible wrap;
wherein the plurality of heat sensors is electrically coupled to the control unit; and
wherein the at least one non-transitory memory comprises stored instructions, which when executed by the one or more processors, causes the controller to:
reduce or terminate power to the at least one heating element to keep a realized temperature as sensed by the plurality of heat sensors below a maximum temperature,
ramp power to the at least one heating element to provide primarily conductive heat perceived by the user,
decrease power to the at least one heating element to provide primarily infrared radiation heat, and
wherein a maximum power applied is at least 30% greater than normal operating power.

16. A method of assisting a user, the method comprising:
applying a portable, battery-powered flexible wrap to a portion of the user's body, wherein the flexible wrap comprises at least one heating element that has at least two modes of heating: conductive and radiant;
switching between primary, with respect to a user's perception, heat sources applied to the user, wherein the switching includes:
applying primarily conductive heat to the user with at least one heating element for a first period time sufficient for the user to sense the application of heat, and
applying primarily radiant heat to the user for a second period of time;
wherein the flexible wrap includes at least one temperature sensor; and
using the at least one temperature sensor to monitor a temperature and limiting power to the at least one heating element to avoid burning or irritating the user.

17. The method of claim 16, wherein the at least one heating element comprises a conductive heating element and a radiant heating element.

18. The method of claim 16, further comprising placing arcuate members in the flexible wrap so that blood flow channels are formed when the flexible wrap is applied.

19. The method of claim 16, wherein applying primarily conductive heat comprises ramping conductive heat such that a temperature versus time graph of has a slope in a range of 0.75 to 2.4 Fahrenheit/Second.

20. A portable recovery system for a user comprising:
a flexible wrap sized and configured to surround at least a portion of the user's body, the flexible wrap having a first side and a second side, wherein the first side is outward facing when in an applied position and the second side is inward facing when in the applied position;

a flexible-wrap fastener coupled to the flexible wrap for releaseably securing the flexible wrap around the portion of the user's body;

at least one heating element coupled to the flexible wrap;

a control unit coupled to the flexible wrap and to the at least one heating element;

a power source coupled to the flexible wrap and electrically coupled to the at least one heating element and the control unit;

wherein the control unit controls the application of heat by the at least one heating element and wherein the control unit and at least one heating element are configured to apply at least two modes of heat: conductive heat and radiant heat and to vary power applied to the heating element to vary relative levels of conductive heat and radiant heat such that in a first mode of operation the at least one heater is configured to primarily provide conductive heat to the user and in a second mode operation the at least one heater is configured to primarily provide radiant heat to the user.

21. The portable recovery system of claim 20, wherein the control unit comprises at least one processor and at least one non-transitory memory; and wherein the at least one non-transitory memory comprises stored instructions, which when executed by the one or more processors, causes the controller to:
to ramp power to the at least one heating element to provide primarily conductive heat perceived by the user, and
to decrease power to the at least one heating element to provide primarily perceivable infrared radiation heat.

22. The portable recovery system of claim 20, wherein the control unit comprises at least one processor and at least one non-transitory memory;

wherein the at least one non-transitory memory comprises stored instructions, which when executed by the one or more processors, causes the controller to:
to ramp power to the at least one heating element to provide primarily conductive heat perceived by the user, and
to decrease power to the at least one heating element to provide primarily infrared radiation heat;
wherein the control unit with its non-transitory memory is programmed to apply power to the at least one heating element to ramp heat with power that is at least 30% greater than normal operating power.

23. The portable recovery system of claim 20, wherein the control unit comprises at least one processor and at least one non-transitory memory;

wherein the at least one non-transitory memory comprises stored instructions, which when executed by the one or more processors, causes the controller to:
to ramp power to the at least one heating element to provide primarily conductive heat perceived by the user, and
thereafter to decrease power to the at least one heating element; and
wherein the control unit with its non-transitory memory is programmed to apply power to the at least one heating element to ramp heat such that a temperature versus time graph has a slope in the range of 0.7 to 2.4 degrees Fahrenheit/Second.

* * * * *